United States Patent
Kubo

(10) Patent No.: US 8,364,415 B2
(45) Date of Patent: Jan. 29, 2013

(54) MELTING CURVE ANALYZING METHOD AND MELTING CURVE ANALYZING DEVICE

(75) Inventor: Kosuke Kubo, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 330 days.

(21) Appl. No.: 12/810,250

(22) PCT Filed: Dec. 25, 2008

(86) PCT No.: PCT/JP2008/073535
§ 371 (c)(1),
(2), (4) Date: Jun. 23, 2010

(87) PCT Pub. No.: WO2009/081965
PCT Pub. Date: Jul. 2, 2009

(65) Prior Publication Data
US 2010/0280789 A1    Nov. 4, 2010

(30) Foreign Application Priority Data
Dec. 26, 2007    (JP) ................................ 2007-334975

(51) Int. Cl.
*G06F 19/00*    (2011.01)
*G06F 15/00*    (2006.01)

(52) U.S. Cl. ............................................. 702/19; 700/1

(58) Field of Classification Search ........................ None
See application file for complete search history.

(56) References Cited

FOREIGN PATENT DOCUMENTS

| JP | 6-324029 | 11/1994 |
|---|---|---|
| JP | 2005-58107 | 3/2005 |
| JP | 2006-170647 | 6/2006 |
| JP | 2007-282512 | 11/2007 |

OTHER PUBLICATIONS

Robinson et al. Rapid, Sensitive, and Discriminating Identification of *Naegleria* spp. by Real-Time PCR and Melting-Curve Analysis Applied and Environmental Microbiology vol. 72, pp. 5857-5863 (2006).*

Loeffler, et al., "Rapid Detection of Point Mutations by Fluorescence Resonance Energy Transfer and Probe Melting Curves in *Candida* Species", Clinical Chemistry 2000, vol. 46, No. 5, pp. 631-635.

* cited by examiner

*Primary Examiner* — John S Brusca
(74) *Attorney, Agent, or Firm* — Morgan, Lewis & Bockius LLP

(57) ABSTRACT

The present invention provides a melting curve analyzing method that can automatically analyze whether or not a peak is present in at least one of two temperature ranges. A signal differential value (A) having a maximum absolute value is searched for among signal differential values at respective temperatures. When a temperature ($t_1$) indicating (A) is included in a temperature range ($T_1$) that is either one of a predetermined temperature range $T_H$ and a predetermined temperature range $T_L$, it is determined that (A) is a first peak. Further, a signal differential value (C) that is a first signal differential value after the absolute value changed from decreasing to increasing and a signal differential value (D) having an absolute value that is greatest next to the absolute value of (A) are searched for. When $X=(A-C)/(D-C)$ satisfies a condition [X<predetermined threshold value] and a temperature ($t_2$) indicating (D) is included in a temperature range ($T_2$), it is determined that the signal differential value (D) is a second peak. When X satisfies a condition [X≧predetermined threshold value], $Y=Y_1/Y_2$ is calculated from an integral value ($Y_1$) of signal differential values in the temperature range ($T_1$) and an integral value ($Y_2$) of signal differential values in the temperature range ($T_2$). When Y satisfies a condition [$1 \leq Y \leq$predetermined threshold value], it is determined that (D) is the second peak.

17 Claims, 9 Drawing Sheets

MELTING CURVE ANALYZING METHOD AND MELTING CURVE ANALYZING DEVICE

TECHNICAL FIELD

The present invention relates to a method for analyzing a melting curve, a system for analyzing a melting curve, a device for analyzing a melting curve, a computer program that can execute the analyzing method on a computer, and an electronic medium storing the computer program.

BACKGROUND ART

In recent years, as a method for detecting a mutation or a polymorphism in a gene, a method for analyzing a melting curve of a double-stranded nucleic acid composed of a target nucleic acid and a probe (a melting curve analysis method) has been employed widely. According to the melting curve analysis method, by analyzing the presence or absence of a peak at a melting temperature (Tm) of the double strand in a melting curve, the determination of a polymorphism in a gene or the detection of the presence or absence of a mutation in a gene becomes possible.

A Tm generally is as defined below. The absorbance at 260 nm increases as a solution containing a double-stranded DNA is heated. This increase is caused by the fact that the hydrogen bond between both the strands in a double-stranded DNA is released by heating, and the double-stranded DNA is dissociated into single-stranded DNAs (melting of DNA). When every double-stranded DNA is dissociated into single-stranded DNAs, the solution exhibits an absorbance about 1.5 times as large as the absorbance at the time when the heating was initiated (the absorbance of the solution containing only the double-stranded DNA), whereby it can be determined that the melting is completed. Based on this phenomenon, a melting temperature Tm (° C.) generally is defined as a temperature at the time when the amount of increase in absorbance reaches 50% of the total amount of increase in absorbance.

By utilizing such nature of a double-stranded DNA, a polymorphism or a mutation in a target site can be detected in the following manner, for example. That is, it can be achieved by the method in which, using a mutant-type detection probe that is complementary to a target nucleic acid sequence containing a mutant type target site, a double-stranded nucleic acid composed of a single-stranded nucleic acid to be analyzed and the probe is formed, the formed double-stranded nucleic acid is heat-treated, the dissociation of the double strand with temperature increase is detected by measuring signal values such as absorbance and the like, and the presence or absence of a mutation in the target site is determined by the behavior of the obtained signal values (ref. Non Patent Citation 1 and Patent Citation 1). The Tm value becomes higher as the homology of a double-stranded nucleic acid becomes higher and becomes lower as the homology of a double-stranded nucleic acid becomes lower. Thus, as evaluation criteria, a Tm value of a double-stranded DNA composed of a target nucleic acid sequence with a mutant-type target site and a mutant-type detection probe that is 100% complementary to the target nucleic acid sequence and a Tm value of a double-stranded DNA composed of a nucleic acid sequence with a wild-type target site and the mutant-type detection probe are determined previously. Since the Tm value becomes higher as the homology of a double-stranded nucleic acid becomes higher as described above, i.e., the Tm value in the case where the target site is of a mutant type (hereinafter, also referred to as "$Tm_m$ value") is relatively high and the latter, i.e., the Tm value in the case where the target site is of a wild type (hereinafter, also referred to as "$Tm_w$ value) is relatively low. Subsequently, a melting curve of the double-stranded nucleic acid composed of the single-stranded nucleic acid to be analyzed and the mutant-type detection probe is prepared, and whether a peak is present at the previously determined $Tm_m$ value or at the previously determined $Tm_w$ value is checked. When the peak is present at around the $Tm_m$ value, the nucleic acid sequence is a 100% match to the mutant-type detection probe, whereby the single-stranded nucleic acid to be analyzed can be determined as having a mutant-type polymorphism. On the other hand, when the peak is present at around the $Tm_w$ value, the nucleic acid sequence is a mismatch to the mutant-type detection probe in a single base, whereby the single-stranded nucleic acid to be analyzed can be determined as having a wild-type polymorphism.

Non Patent Citation 1: Clinical Chemistry, 2000 46 (5): p. 631-635

Patent Citation 1: JP 2005-58107 A

DISCLOSURE OF INVENTION

However, the following problems are seen in conventional methods. That is, the conventional methods do not go beyond preparing a graph of a melting curve showing the relation between temperatures and signal values showing the molten states of a sample at the respective temperatures or differential values of the signal values (hereinafter referred to as "signal differential value"). Conducting visual observation from the melting curve, for example, is the only way to determine whether a polymorphism is of a wild type or of a mutant type. However, since specialized knowledge is required in order to make such determination as to the polymorphism, it is difficult to determine the polymorphism easily based on the melting curve, for example. Further, in the case of visual observation, the fact that criteria of determination vary between individuals has been perceived as a problem. Therefore, it is difficult to expand the application of a gene analysis and a gene diagnosis utilizing the melting curve analysis to the field of general analysis and diagnosis. Further, it is also difficult to analyze multiple specimens all at once from the viewpoint of its specialty or the like. It is considered that the foregoing problems occur not only in gene analysis, but also in the case where it is necessary to determine whether or not a peak is in a predetermined range of a melting curve.

Hence, the present invention is intended to provide an automatable melting curve analyzing method that allows whether or not a peak is present in at least one of two temperature ranges in a melting curve of a sample to be analyzed easily. Further, the present invention is intended to provide a melting curve analyzing system, a melting curve analyzing device, a program, and an electronic medium, each for executing the foregoing melting curve analyzing method.

In order to achieve the aforementioned object, the melting curve analyzing method of the present invention is a melting curve analyzing method for analyzing whether or not a peak is present in at least one of a relatively high predetermined temperature range ($T_H$) and a relatively low predetermined temperature range ($T_L$) in a melting curve of a sample, including:

a step of providing differential values of signal values showing molten states of the sample at respective temperatures;

a step of searching for a first peak candidate by searching for a signal differential value (A) having a maximum absolute value in the signal differential values at the respective temperatures as the first peak candidate; and a step of determining a first peak by determining that the signal differential value (A) is the first peak when a temperature ($t_1$) indicating the signal differential value (A) is included in a temperature range ($T_1$) that is either the temperature range ($T_H$) or the temperature range ($T_L$) and there is no peak when the temperature ($t_1$) indicating the signal differential value (A) is not included in either the temperature range ($T_H$) or the temperature range ($T_L$).

According to the present invention, the presence or absence of a peak in at least one of the temperature range ($T_H$) and the temperature range ($T_L$) in the melting curve can be analyzed by searching for a signal differential value having a maximum absolute value and determining whether or not a temperature indicating the signal differential value is in the temperature range ($T_H$) or the temperature range ($T_L$) as described above. Therefore, it becomes possible to avoid the conventional problems that criteria of determination vary between individuals who conduct analyses and specialized knowledge is required. Thus, it becomes possible to analyze a melting curve easily, and also to automate the analysis. In particular, by incorporating the system of the present invention in a conventional gene analysis device or the like, not only determining a genotype, but also conducting an operation from amplification of a nucleic acid to determination of a genotype in a fully automated manner becomes possible, for example. Therefore, for example, the application of the present invention can be used also in the field of general analysis and diagnosis, and the present invention allows the analysis with respect to a large number of specimens to be conducted easily. Thus, it can be said that the present invention is very useful technology especially in the field of gene analysis.

BEST MODE FOR CARRYING OUT THE INVENTION

Figure 1:
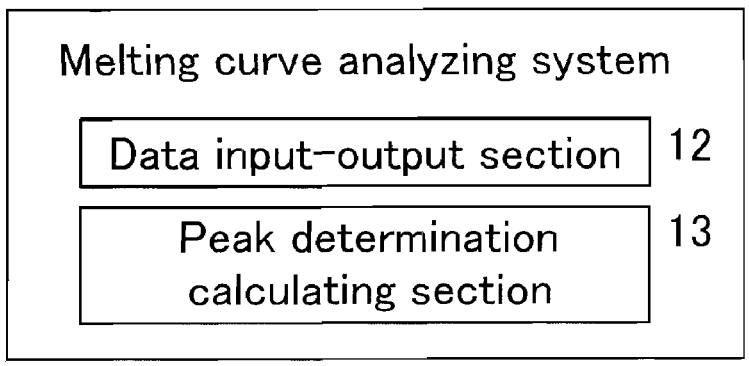
FIG. 1 shows an overall configuration of one example of a stand-alone type device using a system of the present invention.

In the present invention, the sample is not particularly limited as long as, for example, the sample is required to be analyzed as to whether or not a peak is present in a predetermined temperature range in a melting curve. Specific examples of the sample include a double-stranded nucleic acid. The double-stranded nucleic acid is not particularly limited, and examples thereof include a double strand composed of a DNA and a DNA, a double strand composed of an RNA and an RNA, a double strand composed of a DNA and an RNA, and the like. Further, the nucleic acid sequences of the respective single strands in the double-stranded nucleic acid may contain a natural nucleic acid, a non-natural nucleic acid such as a peptide nucleic acid or the like, or both of these nucleic acids.

In the present invention, signals showing the molten states of a sample may be generated by non-melting of the sample, and the generation of the signals may be suppressed by melting of the sample, or on the other hand, the generation of the signals may be suppressed by non-melting of the sample, and the signals may be generated by melting of the sample, for example. In the present invention, the signal differential value may be represented by, for example, "dF/dT" or "−dF/dT". The dF shows the amount of change in signal value, and the dT shows the amount of change in time. When the generation of the signals is suppressed by melting of the sample, a valley-shaped peak is shown in the melting curve representing the signal differential values by "dF/dT", and a mountain-shaped peak is shown in the melting curve representing the signal differential values by "−dF/dT". On the other hand, when the signals are generated by melting of the sample, a mountain-shaped peak is shown in the melting curve representing the signal differential values by "dF/dT", and a valley-shaped peak is shown in the melting curve representing the signal differential values by "−dF/dT". Regardless of whether signals are generated by either melting or non-melting of a sample, and whether signal differential values are represented by either of the formulae, the magnitude of the peak can be evaluated by the magnitude of the absolute value of the signal differential value, for example.

In the present invention, the type of the signal value is not particularly limited, and examples thereof include an absorbance (an absorption intensity), a fluorescent intensity, and the like. When the melting curve analyzing method of the present invention is intended to analyze a melting curve of a double-stranded nucleic acid, the signal values can be, for example, the absorbance at 260 nm, which is increased by melting of a double-stranded nucleic acid, as described above, for example. When a fluorescent substance is used, the signal values may be, for example, intensities of fluorescence that is emitted by irradiation of excitation light depending on the fluorescent substance. The fluorescent substance may generate fluorescence by formation (non-melting) of a double strand or melting of the double strand. Specific examples of the fluorescent substance include intercalaters such as ethidium bromide and SYBR (registered trademark) Green. These fluorescent substances generally generate fluorescence by formation (non-melting) of a double strand and the generation of fluorescence is suppressed by melting of the double strand. In addition, the fluorescent substance may bind to at least one of single-stranded nucleic acids composing a double-stranded nucleic acid. The single-stranded nucleic acid with the fluorescent substance binding thereto can be, for example, a so-called fluorescence quenching probe such as Qprobe (registered trademark) known as a guanine quenching probe. In the fluorescence quenching probe, generally, quenching of fluorescence occurs by formation of a double strand and the fluorescence is generated by melting of the double strand. It is to be noted that the present invention is characterized by the processing of signal values, and the type of the signals and the like are not limited at all.

<Melting Curve Analyzing Method>

The melting curve analyzing method of the present invention is, as described above, a melting curve analyzing method for analyzing whether or not a peak is present in at least one of a relatively high predetermined temperature range ($T_H$) and a relatively low predetermined temperature range ($T_L$) in a melting curve of a sample, including:

a step of providing differential values of signal values showing molten states of the sample at respective temperatures;

a step of searching for a first peak candidate by searching for a signal differential value (A) having a maximum absolute value in the signal differential values at the respective temperatures as the first peak candidate; and a step of determining a first peak by determining that the signal differential value (A) is the first peak when a temperature ($t_1$) indicating the signal differential value (A) is included in a temperature range ($T_1$) that is either one of the temperature range ($T_H$) and the temperature range ($T_L$) and there is no peak when the temperature ($t_1$) indicating the signal differential value (A) is not included in either the temperature range ($T_H$) or the temperature range ($T_L$).

In the present invention, the first peak means a peak present in either the temperature range ($T_H$) or the temperature range ($T_L$) and indicating a signal differential value having a maximum absolute value.

Further, for example, the melting curve analyzing method of the present invention can also analyze whether or not a peak is present in each one of the relatively high predetermined temperature range ($T_H$) and the relatively low predetermined temperature range ($T_L$) by including the steps such as below. In this case, the present invention can also be referred to as a melting curve analyzing method for further analyzing, when it is determined that the first peak is present in either one of the temperature range ($T_H$) and the temperature range ($T_L$), whether or not a second peak is present in the other temperature range in which the first peak is not present. In the present invention, the second peak means a peak present in the other one of the temperature range ($T_H$) and the temperature range ($T_L$), different from the temperature range ($T_1$) in which the first peak is present and showing a signal differential value having an absolute value that is greatest next to the absolute value of the first peak.

The melting curve analyzing method of the present invention preferably further includes:

a step of searching for a second peak candidate, the step including: conducting a search from the temperature range ($T_1$) that is one of the temperature range ($T_H$) and the temperature range ($T_L$) in which the temperature ($t_1$) is included toward a temperature range ($T_2$) that is the other one thereof with the temperature ($t_1$) indicating the signal differential value (A) as a starting point, to find a signal differential value (C) lying immediately before or after an absolute value of a signal differential value changes from decreasing to increasing and having a minimum absolute value, and a signal differential value (D) that is to be a second peak candidate lying immediately before or after an absolute value of a signal differential value changes from increasing to decreasing and having an absolute value that is greatest next to the absolute value of the signal differential value (A) among the signal differential values at the respective temperatures; and a first step of determining a second peak by determining that there is no second peak when the signal differential value (C) and the signal differential value (D) are not present.

Alternatively, in the second peak candidate searching step, a search may be conducted from the temperature range ($T_1$) that is one of the temperature range ($T_H$) and the temperature range ($T_L$) in which the temperature ($t_1$) is included toward a temperature range ($T_2$) that is the other one thereof with the temperature ($t_1$) indicating the signal differential value (A) being as a starting point, to find a signal differential value (C) lying immediately before or after an absolute value of a signal differential value changes from decreasing to increasing (the signal differential value (C) lying immediately after an absolute value of a signal differential value changes from decreasing to increasing is a first signal differential value after an absolute value of a signal differential value changed from decreasing to increasing), and, as a second peak candidate, a signal differential value (D) that is a first signal differential value after the absolute value further increased to be greatest next to the absolute value of the signal differential value (A) among the signal differential values at the respective temperatures.

The second peak candidate searching step and the first second-peak determining step preferably are conducted when the first peak was determined in the above-described first peak determining step. Further, in the first second-peak determining step, it can be determined that the signal differential value (D) is the second peak when the signal differential value (C) and the signal differential value (D) are present, for example.

When the signal differential value (C) and the signal differential value (D) are present, the melting curve analyzing method of the present invention preferably further includes:

a step of calculating X by performing calculation of the formula "$X=(A-C)/(D-C)$" using the signal differential value (A), the signal differential value (C), and the signal differential value (D); and a second step of determining a second peak by determining that the signal differential value (D) is the second peak when X satisfies a condition [X<predetermined threshold value] and a temperature ($t_2$) indicating the signal differential value (D) is included in the other temperature range ($T_2$) and there is no second peak when X satisfies the condition [X<predetermined threshold value] and the temperature ($t_2$) indicating the signal differential value (D) is not included in the other temperature range ($T_2$).

For example, when X satisfies a condition [X≧threshold value], the melting curve analyzing method of the present invention preferably further includes:

a step of calculating an integral value ($Y_1$) of signal differential values in the one temperature range ($T_1$) including the temperature ($t_1$) by integrating the signal differential values in the one temperature range ($T_1$) and an integral value ($Y_2$) of signal differential values in the other temperature range ($T_2$) including the temperature ($t_2$) by integrating the signal differential values in the other temperature range ($T_2$);

a step of calculating Y by performing calculation of the formula "$Y=Y_1/Y_2$" using the integral value ($Y_1$) of the signal differential values in the one temperature range ($T_1$) and the integral value ($Y_2$) of the signal differential values in the other temperature range ($T_2$); and a third step of determining a second peak by determining that the signal differential value (D) is the second peak when Y satisfies a condition [1≦Y≦predetermined threshold value] and there is no second peak when Y satisfies a condition [Y>predetermined threshold value] or a condition [Y<1].

Specific examples of the melting curve analyzing method for analyzing whether or not a peak is present in each one of the temperature range ($T_H$) and the temperature range ($T_L$) include the following method. That is, the method is a melting curve analyzing method for analyzing whether or not a peak is present in each one of the relatively high predetermined temperature range ($T_H$) and the relatively low predetermined temperature range ($T_L$) in the melting curve of a sample, including:

a step of providing differential values of signal values showing molten states of the sample at respective temperatures;

a step of searching for a first peak candidate by searching for a signal differential value (A) having a maximum absolute value in the signal differential values at the respective temperatures as the first peak candidate; and a step of determining a first peak by determining that the signal differential value (A) is the first peak when a temperature ($t_1$) indicating the signal differential value (A) is included in a temperature range ($T_1$) that is either one of the temperature range ($T_H$) and the temperature range ($T_L$) and there is no peak when the temperature ($t_1$) indicating the signal differential value (A) is not included in either the temperature range ($T_H$) or the temperature range ($T_L$). When the first peak is present, the method further includes:

a step of searching for a second peak candidate, the step including: conducting a search from the temperature range ($T_1$) that is one of the temperature range ($T_H$) and the temperature range ($T_L$) in which the temperature ($t_1$) is included toward a temperature range ($T_2$) that is the other one thereof with the temperature ($t_1$) indicating the signal differential value (A) as a starting point, to find a signal differential value (C) lying immediately before or after an absolute value of a signal differential value changes from decreasing to increasing and having a minimum absolute value, and a signal differential value (D) that is to be a second peak candidate lying immediately before or after an absolute value of a signal differential value changes from increasing to decreasing and having an absolute value that is greatest next to the absolute value of the signal differential value (A) among the signal differential values at the respective temperatures; and a first step of determining a second peak by determining that the signal differential value (D) is the second peak candidate when the signal differential value (C) and the signal differential value (D) are present and there is no second peak when the signal differential value (C) and the signal differential value (D) are not present. When the signal differential value (C) and the signal differential value (D) are present, the method further includes:

a step of calculating X by performing calculation of the following formula using the signal differential value (A), the signal differential value (C), and the signal differential value (D):

$$X=(A-C)/(D-C); \text{ and}$$

a second step of determining a second peak by determining that the signal differential value (D) is the second peak when X satisfies a condition [X<predetermined threshold value] and a temperature ($t_2$) indicating the signal differential value (D) is included in the other temperature range ($T_2$) and there is no second peak when X satisfies the condition [X<predetermined threshold value] and the temperature ($t_2$) indicating the signal differential value (D) is not included in the other temperature range ($T_2$). When X satisfies a condition [X≧predetermined threshold value], the method further includes:

a step of calculating an integral value ($Y_1$) of signal differential values in the one temperature range ($T_1$) including the temperature ($t_1$) by integrating the signal differential values in the one temperature range ($T_1$) and an integral value ($Y_2$) of signal differential values in the other temperature range ($T_2$) including the temperature ($t_2$) by integrating the signal differential values in the other temperature range ($T_2$);

a step of calculating Y by performing calculation of the following formula using the integral value ($Y_1$) of the signal differential values in the one temperature range ($T_1$) and the integral value ($Y_2$) of the signal differential values in the other temperature range ($T_2$):

$$Y=Y_1/Y_2; \text{ and}$$

a third step of determining a second peak by determining that the signal differential value (D) is the second peak when Y satisfies a condition [1≦Y≦predetermined threshold value] and there is no second peak when Y satisfies a condition [Y>predetermined threshold value] or a condition [Y<1].

Hereinafter, the melting curve analyzing method of the present invention will be explained with reference to an example where a sample is a double-stranded nucleic acid. Specifically, the double-stranded nucleic acid is a double-stranded nucleic acid composed of a target nucleic acid having a target site and a nucleic acid that can hybridize to the target site (hereinafter referred to as "detection nucleic acid"). By analyzing a melting curve of this double-stranded nucleic acid with the method of the present invention, it is possible to analyze the polymorphism in the target site. It is to be noted that the present invention is not limited to this example.

Differential Value Providing Step

First, differential values of signal values (signal differential values) showing molten states of a double-stranded nucleic acid at respective temperatures are provided.

The signal differential values may be, for example, the values previously calculated, or the values calculated from signal values in the above-described step. Further, the signal differential values are provided, for example, in the wide temperature range including the relatively high temperature range ($T_H$) and the relatively low temperature range ($T_L$).

Each of the temperature range ($T_H$) and the temperature range ($T_L$) preferably includes a Tm value as will be described later. The temperature range ($T_H$) preferably includes a $Tm_H$ value indicating a relatively high temperature, and the temperature range ($T_L$) preferably includes a $Tm_L$ value indicating a relatively low temperature.

Temperature widths of the temperature range ($T_H$) and the temperature range ($T_L$) are not particularly limited. For example, it is preferable that there is a gap between the temperature range ($T_H$) and the temperature range ($T_L$), i.e., between the lower limit of the temperature range ($T_H$) and the upper limit of the temperature range ($T_L$). As a specific example, the difference between the lower limit of the temperature range ($T_H$) and the upper limit of the temperature range ($T_L$) preferably is 3° C. or higher and more preferably 5° C. or higher. The upper limit of the difference is not particularly limited, and the lower limit of the temperature range ($T_H$) and the upper limit of the temperature range ($T_L$) can be determined as appropriate depending on, for example, the set value of the difference, the Tm values ($Tm_H$ and $Tm_L$), and the like. Specifically, one example of setting a temperature range ($T_H$) and a temperature range ($T_L$) based on a $Tm_H$ value (for example, 56° C.) and a $Tm_L$ value (for example, 49° C.) will be given. However, the present invention is not limited to this example. When the lower limit of the $T_H$ and the upper limit of the $T_L$ are determined so that the difference between the lower limit of the $T_H$ including the $Tm_H$ value (56° C.) and the upper limit of the $T_L$ including the $Tm_L$ value (49° C.) becomes 3° C., for example, it is preferable to set the lower limit of $T_H$ (54° C.) and the upper limit of the $T_L$ (51° C.) so that the temperature width from the $Tm_H$ value (56° C.) to the lower limit of $T_H$ and the temperature width from the $Tm_L$ value (49° C.) to the upper limit of the $T_L$ are comparable to each other. The upper limit of the $T_H$ is set so that the temperature width from the $Tm_H$ value (56° C.) to the upper limit of $T_H$ becomes comparable to the temperature width (2° C.) of the $Tm_H$ value (56° C.) and the lower limit of the $T_H$ (54° C.) (the upper limit of the $T_H$ is 58° C.). The lower limit of the $T_L$ is set so that the temperature width from the $Tm_L$ value (49° C.) to the lower limit of the $T_L$ becomes comparable to the temperature width from the $Tm_L$ value (49° C.) to the upper limit of the $T_L$ (51° C.) (the lower limit of the $T_L$ is 47° C.).

As to the wide temperature range including the temperature range ($T_H$) and the temperature range ($T_L$), the lower limit thereof is preferably 1° C. to 20° C. lower than the $Tm_L$ value, more preferably 1° C. to 10° C. lower than the $Tm_L$ value, and the upper limit thereof is preferably 1° C. to 20° C. higher than the $Tm_H$ value, more preferably 1° C. to 10° C. higher than the $Tm_H$ value, for example. As a specific example, the temperature range is preferably from [$Tm_L$ value −5]° C. to [$Tm_H$ value +5]° C., more preferably from [$Tm_L$ value −2]° C. to [$Tm_H$ value +2]° C.

The temperature intervals of the signal differential values are not particularly limited, and are, for example, from 0.1° C. to 5° C., preferably from 0.2° C. to 3° C., and more preferably from 0.8° C. to 1.2° C. The temperature intervals may be different from each other (may be random intervals). However, equal intervals to each other are preferred.

The temperature range ($T_H$) preferably includes a $Tm_H$ value indicating a relatively high temperature, and the temperature range ($T_L$) preferably includes a $Tm_L$ value indicating a relatively low temperature. These Tm values can be determined as appropriate depending on the type of the double-stranded nucleic acid to be analyzed. The Tm values can be determined, for example, by the conventionally known MELTCALC software, Nearest Neighbor Method, and the like. In addition, the Tm values also can be determined by actually measuring the Tm values using an authentic preparation of a double-stranded nucleic acid (the same applies hereinafter). A specific example will be given below. However, the present invention is not limited to this example. When, for example, a detection nucleic acid that can hybridize to a mutant-type target site (hereinafter referred to as "a mutant-type detection nucleic acid") is used as the detection nucleic acid, a Tm value of a double-stranded nucleic acid composed of a target nucleic acid having the mutant-type target site and the mutant-type detection nucleic acid and a Tm value of a double-stranded nucleic acid composed of a target nucleic acid having a wild-type target site and the mutant-type detection nucleic acid are determined previously. Since a Tm value becomes higher as the homology of a double-stranded nucleic acid becomes higher, the former Tm value is a $Tm_H$ value, and the latter Tm value is a $Tm_L$ value. In contrast, when a detection nucleic acid that can hybridize to a wild-type target site is used as the detection nucleic acid (hereinafter referred to as "a wild-type detection nucleic acid"), a Tm value of a double-stranded nucleic acid composed of a target nucleic acid having the wild-type target site and the wild-type detection nucleic acid and a Tm value of a double-stranded nucleic acid composed of a target nucleic acid having a mutant-type target site and the wild-type detection nucleic acid are determined previously. Since a Tm value becomes higher as the homology of a double-stranded nucleic acid becomes higher, the former Tm value is a $Tm_H$ value, and the latter Tm value is a $Tm_L$ value.

It is to be noted that the melting curve analyzing method of the present invention further may include: a step of detecting amplification that has been conducted poorly prior to the differential value providing step, for example. A melting curve analysis of a double-stranded nucleic acid generally is conducted by using an amplification product obtained by amplifying an objective template nucleic acid with a nucleic acid amplifying method. However, for example, there are cases where a sequence to be amplified is not present, or a template nucleic acid is not amplified because of a degraded amplification reagent or the like. Therefore, in the present invention, by detecting the amplification that has been conducted poorly before conducting the differential value providing step, it is possible to cancel the analysis to be conducted with respect to a sample in which amplification has not been conducted and also to conduct analysis with respect to only a sample in which amplification has been conducted.

First Peak Candidate Searching Step

Next, a signal differential value (A) having a maximum absolute value is searched for as a first peak candidate among the signal differential values at the respective temperatures.

First Peak Determining Step

Subsequently, whether or not a temperature ($t_1$) indicating the signal differential value (A) is included in a temperature range ($T_1$) that is either the temperature range ($T_H$) or the temperature range ($T_L$) is checked. Then, when the temperature ($t_1$) is included in the temperature range ($T_1$) that is either one of the temperature range ($T_H$) and the temperature range ($T_L$), it is determined that the signal differential value (A) is the first peak. On the other hand, when the temperature ($t_1$) indicating the signal differential value (A) is not included in either the temperature range ($T_H$) or the temperature range ($T_L$), it is determined that there is no peak.

Second Peak Candidate Searching Step

When it is determined that the first peak is present in the first peak determining step, a search for a signal differential value (C) and a signal differential value (D) is conducted subsequently. Specifically, a search is conducted from, as a starting point, the temperature ($t_1$) indicating the signal differential value (A) in the temperature range ($T_1$) that is one of the temperature range ($T_H$) and the temperature range ($T_L$) in which the temperature ($t_1$) is included toward a temperature range ($T_2$) that is the other one of the temperature range ($T_H$) and the temperature range ($T_L$) to find a signal differential value (C) lying immediately before or after the absolute value changes from decreasing to increasing and having a minimum absolute value, and, as a second peak candidate, a signal differential value (D) lying immediately before or after the absolute value changes from increasing to decreasing and having an absolute value that is greatest next to the absolute value of the signal differential value (A) among the signal differential values at the respective temperatures At this time, a search may be conducted from the temperature range ($T_1$) that is one of the temperature range ($T_H$) and the temperature range ($T_L$) in which the temperature ($t_1$) is included toward a temperature range ($T_2$) that is the other one thereof with the temperature ($t_1$) indicating the signal differential value (A) as a starting point, to find a signal differential value (C) that lies immediately before an absolute value of a signal differential value changes from decreasing to increasing or is a first signal differential value after an absolute value of a signal differential value changed from decreasing to increasing, and, as a second peak candidate, a signal differential value (D) that is a first signal differential value after the absolute value further increased to be greatest next to the absolute value of the signal differential value (A) among the signal differential values at the respective temperatures (the same applies hereinafter).

First Second-Peak Determining Step

When it is determined that the signal differential value (C) and the signal differential value (D) are present in the second peak candidate searching step, it is determined that the signal differential value (D) is the second peak candidate. On the other hand, when the signal differential value (C) and the signal differential value (D) are not present, it is determined that there is no second peak.

X Calculating Step

Subsequently, when it is determined that the signal differential value (C) and the signal differential value (D) are present in the second peak candidate searching step, calculation of the following formula is performed using the signal differential value (A), the signal differential value (C), and the signal differential value (D).

$$X=(A-C)/(D-C)$$

Second Second-Peak Determining Step

When X satisfies a condition [X<predetermined threshold value] and a temperature ($t_2$) indicating the signal differential value (D) is included in the other temperature range ($T_2$), it is determined that the signal differential value (D) is the second peak. On the other hand, when X satisfies the condition [X<predetermined threshold value] and the temperature ($t_2$) indicating the signal differential value (D) is not included in the other temperature range ($T_2$), it is determined that there is no second peak. The threshold value can be set as appropriate depending on the type of the signal, the detection wavelength of the signal, the type of a fluorescent substance that generates signals (fluorescence), the type of a gene or a polymorphism to be detected, the sequence of a detection nucleic acid, the composition of a reaction solution at the time when a double-stranded nucleic acid is formed, and the like. The present invention is not characterized by a specific threshold value or a method for setting the specific threshold value and is not limited thereby. One example of the method for setting the threshold value will be described later.

Integral Value Calculating Step

On the other hand, when X satisfies a condition [X≧predetermined threshold value], an integral value ($Y_1$) of signal differential values in the one temperature range ($T_1$) including the temperature ($t_1$) are calculated by integrating the signal differential values in the one temperature range ($T_1$), and an integral value ($Y_2$) of signal differential values in the other temperature range ($T_2$) including the temperature ($t_2$) are calculated by integrating the signal differential values in the other temperature range ($T_2$).

Y Calculating Step

Calculation of the following formula is performed using the integral value ($Y_1$) of the signal differential values in the one temperature range ($T_1$) and the integral value ($Y_2$) of the signal differential values in the other temperature range ($T_2$).

$$Y=Y_1/Y_2$$

Third Second-Peak Determining Step

When Y satisfies a condition [1≦Y≦predetermined threshold value], it is determined that the signal differential value (D) is the second peak. On the other hand, when Y satisfies a condition [Y>predetermined threshold value] or a condition [Y<1], it is determined that there is no second peak. The threshold value can be set as appropriate depending on the type of the signal, the detection wavelength of the signal, the type of a fluorescent substance that generates signals (fluorescence), the type of a gene or a polymorphism to be detected, the sequence of a detection nucleic acid, the composition of a reaction solution at the time when a double-stranded nucleic acid is formed, and the like. The present invention is not characterized by a specific threshold value or a method for setting the specific threshold value and is not limited thereby. One example of the method for setting the threshold value will be described later. In this way, whether or not a peak is present in each one of a predetermined temperature range $T_H$ and a predetermined temperature range $T_L$ in a melting curve can be determined objectively.

When the target nucleic acid is a pair of alleles, it is required to determine whether a polymorphism in the target site is homozygous or heterozygous. In the present invention, when it is determined that there is no second peak in the first second-peak determining step, the second second-peak determining step, and the third second-peak determining step, only the first peak is present, whereby it can be determined that the polymorphism in the target site is homozygous. On the other hand, when it is determined that the signal differential value (D) is the second peak in any of the steps, the first peak and the second peak are present, whereby it can be determined that the polymorphism in the target site is heterozygous.

Further, when the polymorphism is homozygous, it is required to determine whether the polymorphism in the target site is of a wild type or of a mutant type. Therefore, the present invention further may include a step of determining whether a polymorphism is of a wild type or of a mutant type. In this step, in the case where the wild-type detection nucleic acid is used, when the temperature ($t_1$) indicating the signal differential value (A) as the first peak is included in the temperature range ($T_H$), it can be determined that the polymorphism is of a wild type, and when the temperature ($t_1$) is included in the temperature range ($T_L$), it can be determined that the polymorphism is of a mutant type. On the other hand, in the case where the mutant-type detection nucleic acid is used, when the temperature ($t_1$) indicating the signal differential value (A) as the first peak is included in the relatively high predetermined temperature range ($T_H$), it can be determined that the polymorphism is of a mutant type, and when the temperature ($t_1$) is included in the relatively low predetermined temperature range ($T_L$), it can be determined that the polymorphism is of a wild type. As above, it is possible to determine whether a polymorphism in the target site is homozygous or heterozygous and also whether the polymorphism is of a wild type or of a mutant type.

The melting curve analyzing method of the present invention preferably further includes a step of outputting information of the obtained determination results, for example. The determination results can be items as to the presence or absence of the first peak and the second peak, whether the polymorphism is homozygous or heterozygous, whether the polymorphism is of a wild type or of a mutant type, and the like, for example. At the time of output, only the determination results may be outputted, or these determination results may be outputted with a graph of a melting curve, for example.

For example, the present invention further may include a polynomial value calculating step of calculating polynomial values of the signal differential values at the respective temperatures provided in the differential value providing step by performing polynomial calculation of successive signal differential values. By this step, for example, a peak can be made clearer in a melting curve. The polynomial values of the signal differential values at the respective temperatures calculated in this polynomial value calculating step may be used as the signal differential values at the respective temperatures in each step described above.

A method for calculating polynomial values is not particularly limited, and a common method can be employed. Polynomial calculation may be performed by calculating the sum of successive odd numbers of signal differential values, or calculating the sum of successive even numbers of signal differential values. In the case of calculating the sum of odd numbers of signal differential values, for example, as shown in the following formula, a polynomial value ($Q_M$) of a signal differential value ($P_M$) at an arbitrary point (M) in a melting curve can be calculated from the sum of a signal differential value ($P_M$) at an arbitrary point (M: Mth point), q successive signal differential values lying before the arbitrary point (M) as the center, and q successive signal differential values lying after the arbitrary point as the center. M is a positive integer of two or more, and q is a positive integer of one or more.

Polynomial value ($Q_M$)=$P_{M-q}$+$P_{M-q+1}$+ ... + $P_M$+ ... + $P_{M+PM+q-1}$+$P_{M+q}$ In the case of calculating the sum of even numbers of signal differential values, for example, as shown in the following formula, a polynomial value ($Q_M$) of a signal differential value ($P_M$) at an arbitrary point (M) in a melting curve can be calculated from the sum of a signal differential value ($P_M$) at the arbitrary point (M), r successive signal differential values lying before the arbitrary point (M) as the center, and (r+1) successive signal differential values lying after the arbitrary point as the center. M is a positive integer of two or more, and r is a positive integer of zero or more.

Polynomial value ($Q_M$)=$P_{M-r}$+ ... +$P_M$+ ... + $P_{M+(r+1)}$

Alternatively, for example, as shown in the following formula, the polynomial value ($Q_M$) of the signal differential value ($P_M$) at the arbitrary point (M) in a melting curve can be calculated from the sum of a signal differential value ($P_M$) at the arbitrary point (M), (r+1) successive signal differential values lying before the arbitrary point (M) as the center, and r successive signal differential values lying after the arbitrary point as the center. r is a positive integer of zero or more.

Polynomial value ($Q_M$)=$P_{M-(r+1)}$+ ... +$P_M$+ ... + $P_{M+r}$

In polynomial calculation, the number of signal differential values used for calculating a polynomial value at an arbitrary point is not particularly limited. For example, it is preferable that two or more successive signal differential values, more preferably two to nine successive signal differential values, and still more preferably three successive signal differential values are used for polynomial calculation. In the case where polynomial calculation is performed using three successive signal differential values, polynomial calculation is conducted based on the following formula with respect to, in signal differential values at the respective temperatures of n points (n is a positive integer of three or more) provided in the differential value providing step, the signal differential values at the second to (n−1)th temperatures, whereby polynomial values of the signal differential values at the respective temperatures can be calculated. In the following formula, $P_M$ is a signal differential value at an arbitrary point (M) in a melting curve, $P_{M-1}$ is a signal differential value at a point (M−1) that is immediately before the arbitrary point (M), and $P_{M+1}$ is a signal differential value at a point (M+1) that is immediately after the arbitrary point (M). M is a point after the second point, and specifically, a point selected from second to (n−1)th points.

Polynomial value=($P_{m-1}$+$P_M$+$P_{M+1}$)

Figure 12:
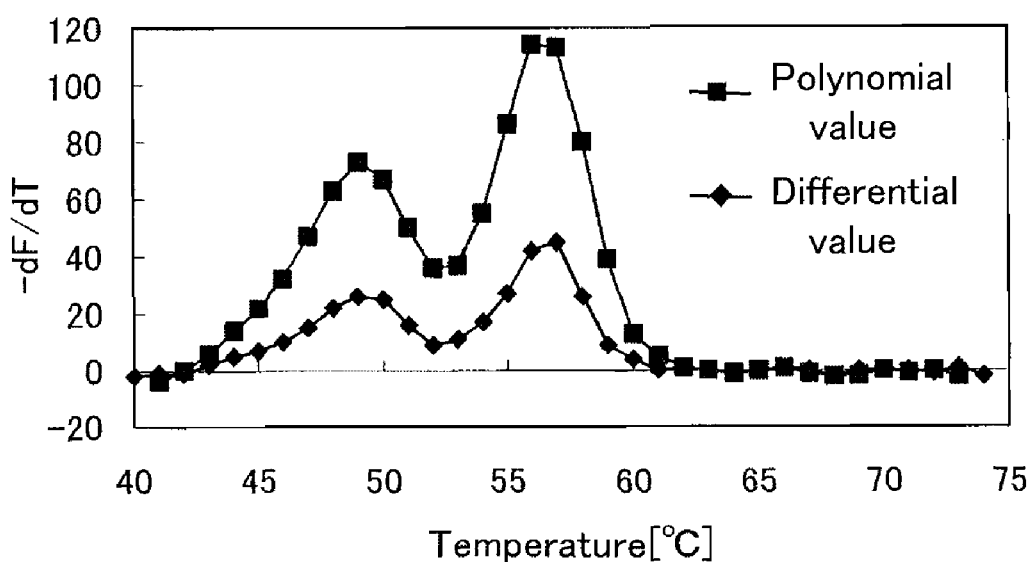
FIG. 12 is yet another graph showing a melting curve in an embodiment of the present invention.

An example of a melting curve in the case where polynomial calculation was performed as above is shown in FIG. 12. FIG. 12 is a graph of a melting curve showing the relation between temperatures and the signal differential values (−dF/dT). In FIG. 12, ♦ are plots indicating signal differential values, and ■ are plots indicating polynomial values of signal differential values. A peak can be made clearer by performing polynomial calculation as above. It is to be noted that the signal differential values, temperatures, and the like in FIG. 12 are merely illustrative and do not limit the present invention (the same applies to other drawings). Further, in the polynomial value calculating step, for example, moving average calculation may be performed with respect to successive signal differential values.

In addition, as the signal differential values in the differential value providing step, previously calculated signal differential values may be used. Alternatively, for example, the signal differential values at respective temperatures may be calculated by differentiating signal values showing molten states of a sample at the respective temperatures. Further, as the signal values, data previously obtained by detection may be used, for example. Alternatively, for example, the signal values may be provided by detection prior to the differential value providing step. Specifically, the melting curve analyzing method further may include, prior to the differential value providing step, the steps of: changing a temperature of the sample (for example, a double-stranded nucleic acid); and detecting signal values showing molten states of the sample at the time of temperature change continuously or intermittently. The temperature changing step may be, for example, a step of heating the sample or a step of cooling the heated sample. However, the heating step is preferred.

The melting curve analyzing method of the present invention will be explained further specifically with reference to melting curves shown in FIGS. 8 to 11 as examples. Each of FIGS. 8 to 11 is a graph of a melting curve showing the relation between temperatures and signal differential values (−dF/dT). In each of FIGS. 8 to 11, temperature is assigned to the X axis, and signal differential value (−dF/dT) is assigned to the Y axis. Further, the relatively low $Tm_L$ value is set to 49° C., the temperature range $T_L$ including the $Tm_L$ value is set to 47° C. to 51° C., the relatively high $Tm_H$ value is set to 56° C., and the temperature range $T_H$ including the $Tm_H$ value is set to 54° C. to 58° C. It is to be noted that these are merely illustrative and do not limit the present invention.

Figure 8:
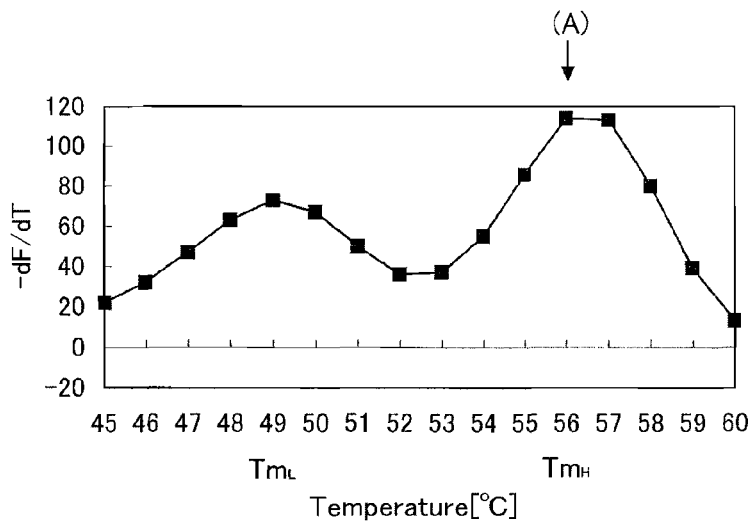
FIG. 8 is a graph showing a melting curve in an embodiment of the present invention.

A melting curve showing the relationship between temperatures and signal differential values at respective temperatures is prepared as shown in FIG. 8, and a signal differential value (A) having a maximum absolute value is searched for. The signal differential value (A) corresponds to a first peak candidate. When the signal differential value (A) is not detected, it is determined that there is no first peak and second peak.

Figure 9:
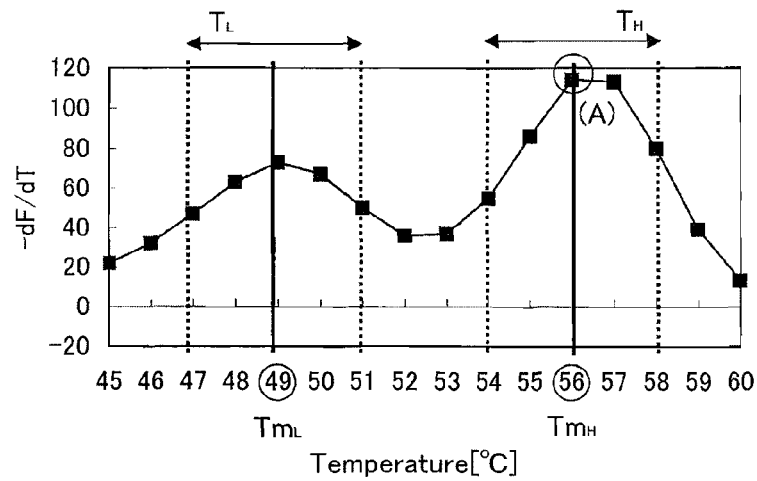
FIG. 9 is another graph showing a melting curve in an embodiment of the present invention.
Figure 10:
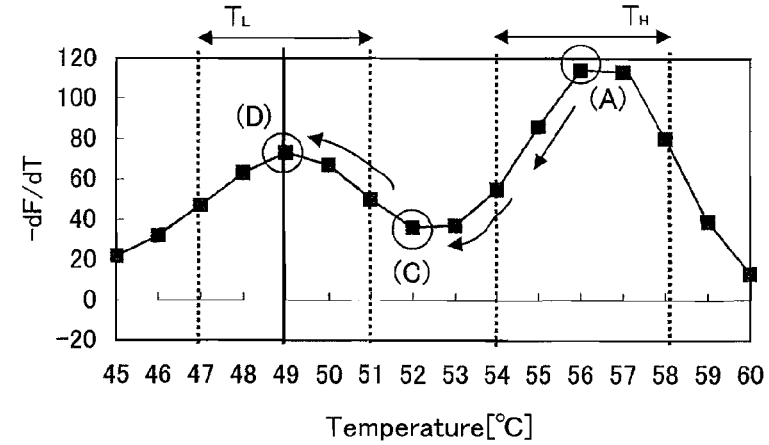
FIG. 10 is yet another graph showing a melting curve in an embodiment of the present invention.
Figure 11:
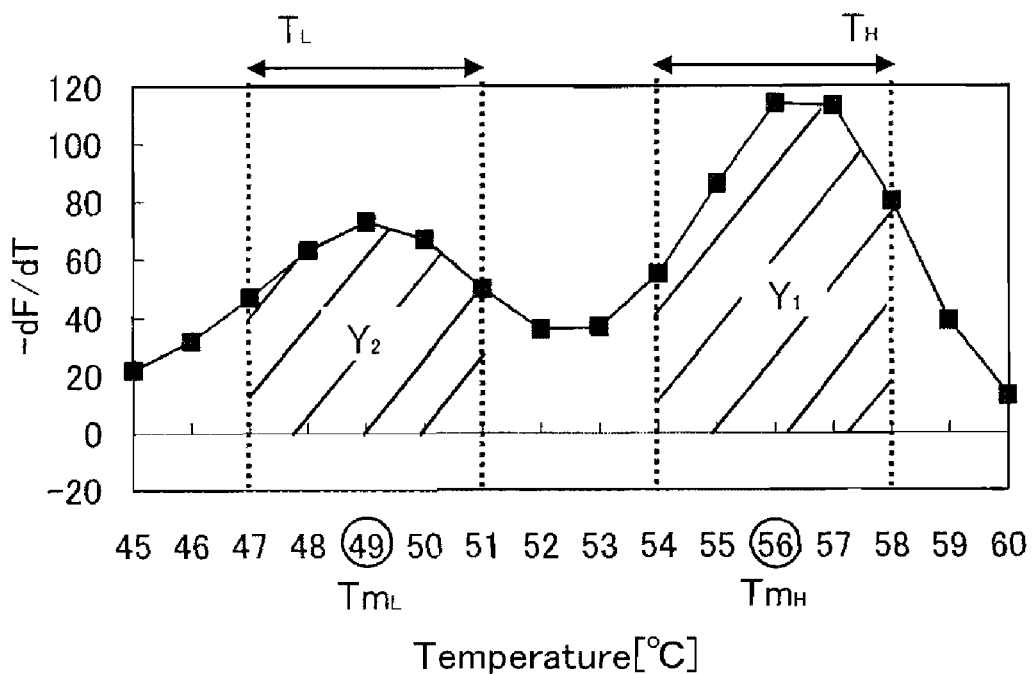
FIG. 11 is yet another graph showing a melting curve in an embodiment of the present invention.

Next, since the temperature 56° C. indicating the signal differential value (A) is included in a temperature range ($T_H$) as shown in FIG. 9, it is determined that the signal differential value (A) is the first peak. Subsequently, as shown in FIG. 10, with the temperature 56° C. indicating the signal differential value (A) being a starting point, a search for a signal differential value (C) lying immediately before the absolute value changes from decreasing to increasing is conducted from the temperature range ($T_H$) toward a temperature range ($T_L$) as indicated by arrows in FIG. 10. In FIG. 10, a signal differential value at 52° C. corresponds to the signal differential value (C). Subsequently, a search for a signal differential value (D) that is a first signal differential value after the absolute value further increased to be greatest next to the absolute value of the signal differential value (A) is conducted from the temperature (52° C.) indicating the signal differential value (C) toward the temperature range ($T_L$) as indicated by an arrow in FIG. 10. In FIG. 10, a signal differential value at 49° C. corresponds to the signal differential value (D) of the second peak candidate. When the signal differential value (C) and the signal differential value (D) are not detected, it is determined that there is no second peak.

Subsequently, calculation of the formula "X=(A−C)/(D−C)" is performed using the signal differential values (A), (C), and (D). When the calculated X satisfies a condition [X<predetermined threshold value], the temperature (49° C.) indicating the signal differential value (D) is included in the temperature range ($T_L$), whereby the signal differential value (D) is determined as the second peak.

On the other hand, when the calculated X satisfies a condition [X≧predetermined threshold value] instead of the condition [X<predetermined threshold value], an integral value ($Y_1$) of signal differential values in the temperature range ($T_H$) is calculated by integrating the signal differential values in the temperature range ($T_H$), and an integral value ($Y_2$) of signal differential values in the temperature range ($T_L$) is calculated by integrating the signal differential values in the temperature range ($T_L$). Hatched areas in FIG. 11 indicate integration ranges of the differential values in the temperature range $T_H$ and the temperature range $T_L$, respectively. Further, calculation of the formula "Y=$Y_1$/$Y_2$" is performed using the integral value ($Y_1$) in the temperature range ($T_H$) and the integral value ($Y_2$) in the temperature range ($T_L$). When Y satisfies a condition [1≦Y≦predetermined threshold value], it is determined that the signal differential value (D) is the second peak. When Y satisfies a condition [Y>predetermined threshold value] or a condition [Y<1], it is determined that there is no second peak.

In the present invention, as described above, the threshold value of X and the threshold value of Y are not limited at all and can be determined as appropriate depending on, for example, the type of a target nucleic acid (gene), the type of a polymorphism, and the like. Hereinafter, a method for setting the threshold values will be described by way of example. However, the present invention is not limited thereto.

Figure 13:
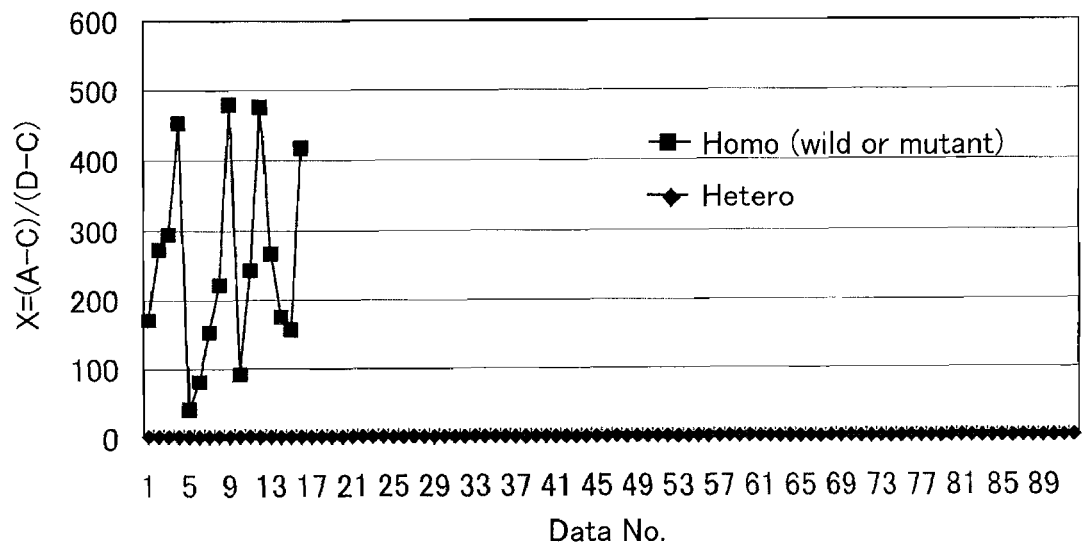
FIG. 13 is a graph showing X calculated from signal differential values in an embodiment of the present invention.

The threshold value of X can be determined as below, for example. Multiple nucleic acid specimens with a known polymorphism (homozygous or heterozygous) in a target site of a predetermined gene previously are provided. Further, from a melting curve relating to a double strand composed of each of the nucleic acid specimens and a detection nucleic acid, signal differential values (A), (C), and (D) are determined and calculation of the formula X=(A−C)/(D−C) is performed in the same manner as described above. Then, a graph plotting Xs of the respective nucleic acid specimens is prepared. One example of this graph is shown in FIG. 13. As can be seen from FIG. 13, Xs of the specimens with the homozygous polymorphism in which only the first peak is detected (■) and Xs of the specimens with the heterozygous polymorphism in which the first peak and the second peak are detected (♦) are distinctly different. Thus, a critical value between the specimens with the homozygous polymorphism and the specimens with the heterozygous polymorphism are determined from this graph, and this value can be set to the threshold value of X.

Figure 14:
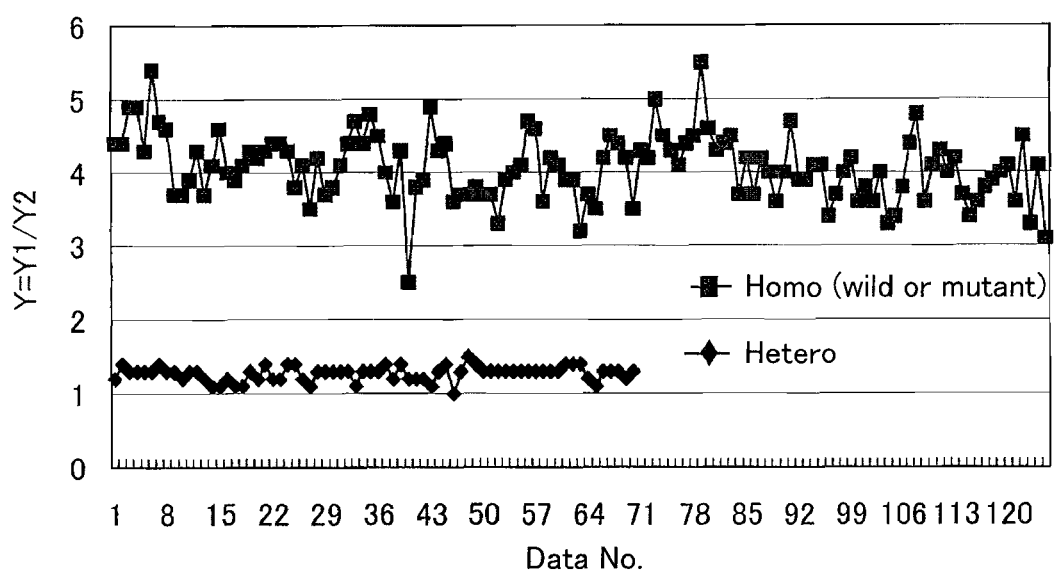
FIG. 14 is a graph showing a ratio of signal integral values in an embodiment of the present invention.

A threshold value of Y also can be determined in the same manner as the method for setting the threshold value of X. Multiple nucleic acid specimens with a known polymorphism (homozygous or heterozygous) in a target site of a predetermined gene are previously provided. Further, an integral value ($Y_1$) in the temperature range T1 and an integral value ($Y_2$) in the temperature range $T_2$ are calculated from a melting curve relating to a double strand composed of each of the nucleic acid specimens and a detection nucleic acid, and calculation of the formula Y=$Y_1$/$Y_2$ is performed. Then, a graph plotting Ys of the respective nucleic acid specimens is prepared. One example of this graph is shown in FIG. 14. As can be seen from FIG. 14, Ys of the specimens with the homozygous polymorphism in which only the first peak is detected (■) and Ys of the specimens the heterozygous polymorphism in which the first peak and the second peak are detected (♦) are distinctly different. Thus, a critical value between the specimens with the homozygous polymorphism and the specimens with the heterozygous polymorphism are determined from this graph, and this value can be set to the threshold value of Y.

The melting curve analyzing method of the present invention can be achieved by, for example, a melting curve analyzing system of the present invention, a melting curve analyzing device of the present invention, running a computer program of the present invention, or the like, which will be described later.

<Second Peak Determining Method>

A second peak determining method of the present invention corresponds to the integral value calculating step, the Y calculating step, and the third second-peak determining step in the above-described melting curve analyzing method of the present invention. According to this method, the presence or absence of a second peak can be determined easily in a melting curve in which it has been determined that a first peak is present.

The second peak determining method of the present invention is a method for determining, when a peak (a first peak) is present in a temperature range ($T_1$) that is either one of a relatively high predetermined temperature range ($T_H$) and a relatively low predetermined temperature range ($T_L$) in a melting curve of a sample, whether or not a peak (a second peak) is present in a temperature range ($T_2$) that is the other one of the temperature range ($T_H$) and the temperature range ($T_L$), including:

a step of providing differential values of signal values showing molten states of the sample at respective temperatures;

a step of calculating an integral value ($Y_1$) of signal differential values in the one temperature range ($T_1$) by integrating the signal differential values in the one temperature range ($T_1$) and an integral value ($Y_2$) of signal differential values in the other temperature range ($T_2$) by integrating the signal differential values in the other temperature range ($T_2$);

a step of calculating Y by performing calculation of the formula "Y=$Y_1$/$Y_2$" using the integral value ($Y_1$) of the signal differential values in the one temperature range ($T_1$) and the integral value ($Y_2$) of the signal differential values in the other temperature range ($T_2$); and a step of determining a second peak by determining that there is the second peak when Y satisfies a condition [1≦Y≦predetermined threshold value] and there is no second peak when Y satisfies a condition [Y>predetermined threshold value] or a condition [Y<1]. It is to be noted that the second peak determining step corresponds to the above-described third second-peak determining step.

The second peak determining method of the present invention further may include the above-described second peak candidate searching step, first second-peak determining step, X calculating step, and the second second-peak determining step prior to the integral value calculating step, for example. That is, the second peak determining method of the present invention further may include, prior to the Y calculating step, conducting a search from the temperature range ($T_1$) in which the temperature ($t_1$) is included toward the other temperature range ($T_2$) with the temperature ($t_1$) indicating the signal differential value (A) being as a starting point, to find a signal differential value (C) lying immediately before or after an absolute value of a signal differential value changes from decreasing to increasing and having a minimum absolute value, and, as a second peak candidate, a signal differential value (D) lying immediately before or after an absolute value of a signal differential value changes from increasing to decreasing and having an absolute value that is greatest next to the absolute value of the signal differential value (A), for example.

Further, the second peak determining method further may include a first second-peak determining step, and in this step, it may be determined that the signal differential value (D) is the second peak candidate when the signal differential value (C) and the signal differential value (D) are present, and it may be determined that there is no second peak when the signal differential value (C) and the signal differential value (D) are not present. When the second peak candidate is determined in this step, the Y calculating step and the third second-peak determining step may be conducted thereafter, and further, the X calculating step and the second second-peak determining step may be conducted.

That is, for example, when the signal differential value (C) and the signal differential value (D) are present, the second peak determining method of the present invention may further include:

a step of calculating X by performing calculation of the formula "X=(A−C)/(D−C)" using the signal differential value (A), the signal differential value (C), and the signal differential value (D); and a second step of determining a second peak by determining that the signal differential value (D) is the second peak when X satisfies a condition [X<predetermined threshold value] and a temperature ($t_2$) indicating the signal differential value (D) is included in the other temperature range ($T_2$) and there is no second peak when X satisfies the condition [X<predetermined threshold value] and the temperature ($t_2$) indicating the signal differential value (D) is not included in the other temperature range ($T_2$). The above-described Y calculating step preferably is conducted when X satisfied a condition [X≧predetermined threshold value].

The second peak determining method of the present invention can be achieved by, for example, a melting curve analyzing system of the present invention, a second peak determining system of the present invention, a melting curve analyzing device of the present invention, running a computer program of the present invention, or the like, which will be described later.

<Melting Curve Analyzing System>

A melting curve analyzing system of the present invention is a system for analyzing whether or not a peak is present in at least one of a relatively high predetermined temperature range ($T_H$) and a relatively low predetermined temperature range ($T_L$) in a melting curve of a sample, including:

a differential value input section for inputting differential values of signal values showing molten states of the sample at respective temperatures;

a first peak candidate searching section for searching for a first peak candidate by searching for a signal differential value (A) having a maximum absolute value in the signal differential values at the respective temperatures inputted by the differential value input section as the first peak candidate; and a first peak determining section for determining a first peak by determining that the signal differential value (A) is the first peak when a temperature ($t_1$) indicating the signal differential value (A) is included in a temperature range ($T_1$) that is either one of the temperature range ($T_H$) and the temperature range ($T_L$) and there is no peak when the temperature ($t_1$) indicating the signal differential value (A) is not included in either the temperature range ($T_H$) or the temperature range ($T_L$).

In addition, the melting curve analyzing system of the present invention also can analyze whether or not a peak is present in each one of a relatively high predetermined temperature range ($T_H$) and a relatively low predetermined temperature range ($T_L$) by including sections such as below, for example. In this case, the present invention also can be referred to as a melting curve analyzing system for analyzing, when it is determined that the first peak is present in either one of the temperature range ($T_H$) and the temperature range ($T_L$), whether or not the second peak is present in the other temperature range in which the first peak is not present.

The melting curve analyzing system of the present invention preferably further includes:

a second peak candidate searching section for conducting a search from the temperature range ($T_1$) that is one of the temperature range ($T_H$) and the temperature range ($T_L$) in which the temperature ($t_1$) is included toward a temperature range ($T_2$) that is the other one thereof with the temperature ($t_1$) indicating the signal differential value (A) being as a starting point, to find a signal differential value (C) lying immediately before or after an absolute value of a signal differential value changes from decreasing to increasing and having a minimum absolute value, and a signal differential value (D) that is to be a second peak candidate lying immediately before or after an absolute value of a signal differential value changes from increasing to decreasing and having an absolute value that is greatest next to the absolute value of the signal differential value (A) among the signal differential values at the respective temperatures inputted by the differential value input section; and a first second-peak determining section for determining a second peak by determining that there is no second peak when the signal differential value (C) and the signal differential value (D) are not present.

When the signal differential value (C) and the signal differential value (D) are present, the signal differential value (D) can be determined as a second peak candidate in the first second-peak determining section Alternatively, the second peak candidate searching section may be a searching section for conducting a search from the temperature range ($T_1$) that is one of the temperature range ($T_H$) and the temperature range ($T_L$) in which the temperature ($t_1$) is included toward a temperature range ($T_2$) that is the other one thereof with the temperature ($t_1$) indicating the signal differential value (A) as a starting point, to find a signal differential value (C) lying immediately before or after an absolute value of a signal differential value changes from decreasing to increasing (the signal differential value (C) lying immediately after an absolute value of a signal differential value changes from decreasing to increasing is a first signal differential value after an absolute value of a signal differential value changed from decreasing to increasing), and, as a second peak candidate, a signal differential value (D) that is a first signal differential value after the absolute value further increased to be greatest next to the absolute value of the signal differential value (A) among the signal differential values at the respective temperatures.

For example, the melting curve analyzing system of the present invention preferably further includes:

an X calculating section for performing calculation of the formula "X=(A−C)/(D−C)" using the signal differential value (A), the signal differential value (C), and the signal differential value (D); and a second second-peak determining section for determining a second peak by determining that the signal differential value (D) is the second peak when X satisfies a condition [X<predetermined threshold value] and a temperature ($t_2$) indicating the signal differential value (D) is included in the other temperature range ($T_2$) and there is no second peak when X satisfies the condition [X<predetermined threshold value] and the temperature ($t_2$) indicating the signal differential value (D) is not included in the other temperature range ($T_2$).

When the signal differential value (C) and the signal differential value (D) are present, whether or not the second peak candidate is the second peak can be determined by these sections.

The melting curve analyzing system of the present invention preferably further includes:

an integral value calculating section for calculating an integral value ($Y_1$) of signal differential values in the one temperature range ($T_1$) including the temperature ($t_1$) by integrating the signal differential values in the one temperature range ($T_1$) and an integral value ($Y_2$) of signal differential values in the other temperature range ($T_2$) including the temperature ($t_2$) by integrating the signal differential values in the other temperature range ($T_2$);

a Y calculating section for performing calculation of the formula "$Y=Y_1/Y_2$" using the integral value ($Y_1$) of the signal differential values in the one temperature range ($T_1$) and the integral value ($Y_2$) of the signal differential values in the other temperature range ($T_2$); and a third second-peak determining section for determining a second peak by determining that the signal differential value (D) is the second peak when Y satisfies a condition [$1 \leq Y \leq$ predetermined threshold value] and there is no second peak when Y satisfies a condition [Y>predetermined threshold value] or a condition [Y<1].

When X calculated in the X calculating section satisfies a condition [$X \geq$ predetermined threshold value], whether the signal differential value (D) is the second peak or not can be determined by these sections.

Specific examples of the melting curve analyzing system for analyzing whether or not a peak is present in each one of the relatively high predetermined temperature range ($T_H$) and the relatively low predetermined temperature range ($T_L$) include the following system. That is, the system is a melting curve analyzing system for analyzing whether or not a peak is present in each one of a relatively high predetermined temperature range ($T_H$) and a relatively low predetermined temperature range ($T_L$) in a melting curve of a sample, including:

a differential value input section for inputting differential values of signal values showing molten states of the sample at respective temperatures;

a first peak candidate searching section for searching for a first peak candidate by searching for a signal differential value (A) having a maximum absolute value in the signal differential values at the respective temperatures inputted by the differential value input section as the first peak candidate;

a first peak determining section for determining a first peak by determining that the signal differential value (A) is the first peak when a temperature ($t_1$) indicating the signal differential value (A) is included in a temperature range ($T_1$) that is either one of the temperature range ($T_H$) and the temperature range ($T_L$) and there is no peak when the temperature ($t_1$) indicating the signal differential value (A) is not included in either the temperature range ($T_H$) or the temperature range ($T_L$);

a second peak candidate searching section for, when the first peak is present, conducting a search from the temperature range ($T_1$) that is one of the temperature range ($T_H$) and the temperature range ($T_L$) in which the temperature ($t_1$) is included toward a temperature range ($T_2$) that is the other one thereof with the temperature ($t_1$) indicating the signal differential value (A) as a starting point, to find a signal differential value (C) lying immediately before or after an absolute value of a signal differential value changes from decreasing to increasing and having a minimum absolute value, and a signal differential value (D) that is to be a second peak candidate lying immediately before or after an absolute value of a signal differential value changes from increasing to decreasing and having an absolute value that is greatest next to the absolute value of the signal differential value (A) among the signal differential values at the respective temperatures inputted by the differential value input section;

a first second-peak determining section for determining a second peak by determining that the signal differential value (D) is the second peak candidate when the signal differential value (C) and the signal differential value (D) are present and there is no second peak when the signal differential value (C) and the signal differential value (D) are not present;

an X calculating section for performing calculation of the following formula using the signal differential value (A), the signal differential value (C), and the signal differential value (D):

$$X=(A-C)/(D-C);$$

a second second-peak determining section for determining that the signal differential value (D) is the second peak when X satisfies a condition [X<predetermined threshold value] and a temperature ($t_2$) indicating the signal differential value (D) is included in the other temperature range ($T_2$) and there is no second peak when X satisfies the condition [X<predetermined threshold value] and the temperature ($t_2$) indicating the signal differential value (D) is not included in the other temperature range ($T_2$);

an integral value calculating section for calculating, when X satisfies a condition [$X \geq$ predetermined threshold value], an integral value ($Y_1$) of signal differential values in the one temperature range ($T_1$) including the temperature ($t_1$) by integrating the signal differential values in the one temperature range ($T_1$) and an integral value ($Y_2$) of signal differential values in the other temperature range ($T_2$) including the temperature ($t_2$) by integrating the signal differential values in the other temperature range ($T_2$);

a Y calculating section for performing calculation of the following formula using the integral value ($Y_1$) of the signal differential values in the one temperature range ($T_1$) and the integral value ($Y_2$) of the signal differential values in the other temperature range ($T_2$):

$$Y=Y_1/Y_2; \text{ and}$$

a third second-peak determining section for determining that the signal differential value (D) is the second peak when Y satisfies a condition [$1 \leq Y \leq$ predetermined threshold value] and there is no second peak when Y satisfies a condition [Y>predetermined threshold value] or a condition [Y<1].

The melting curve analyzing system of the present invention preferably further includes: a differential value calculating section for calculating signal differential values at respective temperatures by differentiating signal values showing molten states of a sample at the respective temperatures.

The melting curve analyzing system of the present invention may further include: a polynomial value calculating section for calculating polynomial values of the signal differential values at the respective temperatures inputted by the differential value input section by performing polynomial calculation of successive signal differential values. It is preferable that the polynomial values of the signal differential values at the respective temperatures calculated in the polynomial value calculating section are used as the signal differential values at the respective temperatures in other sections.

In the melting curve analyzing system of the present invention, the polynomial value calculating section is not particularly limited, and common means can be employed. Polynomial calculation may be performed by calculating the sum of successive odd numbers of signal differential values, or calculating the sum of successive even numbers of signal differential values. In the case of calculating the sum of odd numbers of signal differential values, for example, as shown in the following formula, a polynomial value ($Q_M$) of a signal differential value ($P_M$) at an arbitrary point (M) in a melting curve can be calculated from the sum of a signal differential value ($P_M$) at an arbitrary point (M: Mth point), q successive signal differential values lying before the arbitrary point (M) as the center, and q successive signal differential values lying after the arbitrary point as the center. M is a positive integer of two or more, and q is a positive integer of one or more.

$$\text{Polynomial value } (Q_M) = P_{M-q} + P_{M-q+1} + \ldots + P_M + \ldots + P_{M+q-1} + P_{M+q}$$

In the case of calculating the sum of even numbers of signal differential values, for example, as shown in the following formula, a polynomial value ($Q_M$) of a signal differential value ($P_M$) at an arbitrary point (M) in a melting curve can be calculated from the sum of a signal differential value ($P_M$) at the arbitrary point (M), r successive signal differential values lying before the arbitrary point (M) as the center, and (r+1) successive signal differential values lying after the arbitrary point as the center. M is a positive integer of two or more, and r is a positive integer of zero or more.

$$\text{Polynomial value } (Q_M) = P_{M-(r+1)} + \ldots + P_M + \ldots + P_{M+(r+1)}$$

Alternatively, for example, as shown in the following formula, the polynomial value ($Q_M$) of the signal differential value ($P_M$) at the arbitrary point (M) in a melting curve can be calculated from the sum of a signal differential value ($P_M$) at the arbitrary point (M), (r+1) successive signal differential values lying before the arbitrary point (M) as the center, and r successive signal differential values lying after the arbitrary point as the center. r is a positive integer of zero or more.

$$\text{Polynomial value } (Q_M) = P_{M-(r+1)} + \ldots + P_M + \ldots + P_{M+r}$$

In polynomial calculation, the number of signal differential values used for calculating a polynomial value at an arbitrary point is not particularly limited. For example, it is preferable that two or more successive signal differential values, more preferably two to nine successive signal differential values, and still more preferably three successive signal differential values are used for polynomial calculation. In the case where polynomial calculation is performed using three successive signal differential values, polynomial calculation is conducted based on the following formula with respect to, in signal differential values at the respective temperatures of n points (n is a positive integer of three or more) provided in the differential value providing step, the signal differential values at the second to (n−1)th temperatures, whereby polynomial values of the signal differential values at the respective temperatures can be calculated. In the following formula, $P_M$ is a signal differential value at an arbitrary point (M) in a melting curve, $P_{M-1}$ is a signal differential value at a point (M−1) that is immediately before the arbitrary point (M), and $P_{M+1}$ is a signal differential value at a point (M+1) that is immediately after the arbitrary point (M). M is a point after the second point, and specifically, a point selected from second to (n−1)th points.

$$\text{Polynomial value} = (P_{M-1} + P_M + P_{M+1})$$

The melting curve analyzing system of the present invention preferably further includes: a temperature changing section for changing a temperature of the sample; and a detection section for detecting signal values showing molten states of the sample at the time of temperature change continuously or intermittently. The temperature changing section may be, for example, a heating section for heating the sample or a cooling section for cooling the heated sample. Examples of the temperature changing section include a temperature controller, a heater, a thermal cycler, and the like that can adjust a temperature, and examples of the detection section include a spectrophotometer, a fluorometer, and the like. Further, examples of means including both of the sections include measuring instruments used for a real-time PCR, and the like.

In the melting curve analyzing system of the present invention, preferably, the signals are fluorescence, and the detection section detects the fluorescence, for example.

The melting curve analyzing system of the present invention preferably is a system for analyzing a melting curve of a double-stranded nucleic acid, and the double-stranded nucleic acid preferably is composed of a target nucleic acid having a target site and a nucleic acid that can hybridize to the target site. A polymorphism in the target site preferably is analyzed by analyzing the melting curve of the double-stranded nucleic acid composed of the target nucleic acid having the target site and the nucleic acid that can hybridize to the target site.

In the present invention, in the case where the target nucleic acid is a pair of alleles, when it is determined that there is no second peak, it preferably is determined further that the polymorphism in the target site is homozygous by the first second-peak determining section, the second second-peak determining section, and the third second-peak determining section, and when it is determined that the signal differential value (D) is the second peak, it preferably is determined further that the polymorphism in the target site is heterozygous by the same.

The melting curve analyzing system of the present invention preferably further includes: a polymorphism determining section for determining whether a polymorphism in a target site of the target nucleic acid is of a wild type or of a mutant type, wherein in the case where the nucleic acid that can hybridize to the target site can hybridize to a wild-type target site, it is determined that the polymorphism is of a wild type when the temperature ($t_1$) indicating the signal differential value (A) as the first peak is included in the relatively high predetermined temperature range ($T_H$), and it is determined that the polymorphism is of a mutant type when the temperature ($t_1$) indicating the signal differential value (A) as the first peak is included in the relatively low predetermined temperature range ($T_L$), and in the case where the nucleic acid that can hybridize to the target site can hybridize to a mutant-type target site, it is determined that the polymorphism is of a mutant type when the temperature ($t_1$) indicating the signal differential value (A) as the first peak is included in the relatively high predetermined temperature range ($T_H$), and it is determined that the polymorphism is of a wild type when the temperature ($t_1$) indicating the signal differential value (A) as the first peak is included in the relatively low predetermined temperature range ($T_L$).

The melting curve analyzing system of the present invention preferably further includes an output section for outputting information of the determination results as to the presence or absence of the first peak and the second peak, as to whether a polymorphism is homozygous or heterozygous, as to whether a polymorphism is of a wild type or of a mutant type, and the like, for example. At the time of output, only the determination results may be outputted, or these determination results may be outputted with a graph of a melting curve.

<Network Melting Curve Analyzing System and Terminal Used Therefor>

The melting curve analyzing system of the present invention may be a network system including a terminal and a server that are described below. It is to be noted that the system is the same as the above-described melting curve analyzing system unless otherwise stated. That is, the network melting curve analyzing system of the present invention is a network melting curve analyzing system for analyzing whether or not a peak is present in at least one of a relatively high predetermined temperature range ($T_H$) and a relatively low predetermined temperature range ($T_L$) in a melting curve of a sample, including:

a terminal; and a server, wherein the terminal and the server are connectable through a communication network that is outside of the system, the terminal includes:

a differential value input section for inputting differential values of signal values showing molten states of the sample at respective temperatures;

a terminal-side transmitting section for transmitting information in the terminal to the server through the communication network; and a terminal-side receiving section for receiving the information transmitted from the server through the communication network, the server includes:

a server-side transmitting section for transmitting information in the server to the terminal through the communication network;

a server-side receiving section for receiving the information transmitted from the terminal through the communication network;

a first peak candidate searching section for searching for a first peak candidate by searching for a signal differential value (A) having a maximum absolute value in the signal differential values at the respective temperatures received by the server-side receiving section as the first peak candidate; and a first peak determining section for determining the first peak by determining that the signal differential value (A) is the first peak when a temperature ($t_1$) indicating the signal differential value (A) is included in a temperature range ($T_1$) that is either one of the temperature range ($T_H$) and the temperature range ($T_L$) and there is no peak when the temperature ($t_1$) indicating the signal differential value (A) is not included in either the temperature range ($T_H$) or the temperature range ($T_L$). In the system, at least the signal differential values at the respective temperatures are transmitted from the terminal-side transmitting section to the server-side receiving section, and information of the determination result as to the first peak is transmitted from the server-side transmitting section to the terminal-side receiving section.

In addition, the melting curve analyzing system of the present invention also can analyze whether or not a peak is present in each one of a relatively high predetermined temperature range ($T_H$) and a relatively low predetermined temperature range ($T_L$) by including sections such as below, for example. In this case, the present invention also can be referred to as a melting curve analyzing system for analyzing, when it is determined that the first peak is present in either one of the temperature range ($T_H$) and the temperature range ($T_L$), whether or not the second peak is present in the other temperature range in which the first peak is not present. Further, in this case, the information of the determination result as to the second peak preferably is transmitted from the server-side transmitting section to the terminal-side receiving section in addition to the determination result as to the first peak.

The melting curve analyzing system of the present invention preferably further includes:

a second peak candidate searching section for conducting a search from the temperature range ($T_1$) that is one of the temperature range ($T_H$) and the temperature range ($T_L$) in which the temperature ($t_1$) is included toward a temperature range ($T_2$) that is the other one thereof with the temperature ($t_1$) indicating the signal differential value (A) as a starting point, to find a signal differential value (C) lying immediately before or after an absolute value of a signal differential value changes from decreasing to increasing and having a minimum absolute value, and a signal differential value (D) that is to be a second peak candidate lying immediately before or after an absolute value of a signal differential value changes from increasing to decreasing and having an absolute value that is greatest next to the absolute value of the signal differential value (A) among the signal differential values at the respective temperatures received by the server-side receiving section; and a first second-peak determining section for determining a second peak by determining that there is no second peak when the signal differential value (C) and the signal differential value (D) are not present. When the signal differential value (C) and the signal differential value (D) are present, the signal differential value (D) can be determined as the second peak candidate in the first-second peak determining section.

The melting curve analyzing system of the present invention preferably further includes:

an X calculating section for performing calculation of the formula "X=(A–C)/(D–C)" using the signal differential value (A), the signal differential value (C), and the signal differential value (D); and a second second-peak determining section for determining a second peak by determining that the signal differential value (D) is the second peak when X satisfies a condition [X<predetermined threshold value] and a temperature ($t_2$) indicating the signal differential value (D) is included in the other temperature range ($T_2$) and there is no second peak when X satisfies the condition [X<predetermined threshold value] and the temperature ($t_2$) indicating the signal differential value (D) is not included in the other temperature range ($T_2$). When the signal differential value (C) and the signal differential value (D) are present, whether or not the second peak candidate is the second peak can be determined by these sections.

The melting curve analyzing system of the present invention preferably further includes:

an integral value calculating section for calculating an integral value ($Y_1$) of signal differential values in the one temperature range ($T_1$) including the temperature ($t_1$) by integrating the signal differential values in the one temperature range ($T_1$) and an integral value ($Y_2$) of signal differential values in the other temperature range ($T_2$) including the temperature ($t_2$) by integrating the signal differential values in the other temperature range ($T_2$);

a Y calculating section for performing calculation of the formula "$Y=Y_1/Y_2$" using the integral value ($Y_1$) of the signal differential values in the one temperature range ($T_1$) and the integral value ($Y_2$) of the signal differential values in the other temperature range ($T_2$);

a third second-peak determining section for determining that the signal differential value (D) is the second peak when Y satisfies a condition [$1 \leq Y \leq$ predetermined threshold value] and there is no second peak when Y satisfies a condition [Y>predetermined threshold value] or a condition [Y<1]. When X calculated in the X calculating section satisfies a condition [X$\geq$predetermined threshold value], whether the signal differential value (D) is the second peak or not can be determined by these sections.

Specific examples of the melting curve analyzing system for analyzing whether or not a peak is present in each one of the relatively high predetermined temperature range ($T_H$) and the relatively low predetermined temperature range ($T_L$) include the following system. That is, the system is a network melting curve analyzing system for analyzing whether or not a peak is present in each one of a relatively high predetermined temperature range ($T_H$) and a relatively low predetermined temperature range ($T_L$) in a melting curve of a sample, including:

a terminal; and
a server,
wherein the terminal and the server are connectable through a communication network that is outside of the system, the terminal includes:
a differential value input section for inputting differential values of signal values showing molten states of the sample at respective temperatures;
a terminal-side transmitting section for transmitting information in the terminal to the server through the communication network; and
a terminal-side receiving section for receiving the information transmitted from the server through the communication network, the server includes:
a server-side transmitting section for transmitting information in the server to the terminal through the communication network;
a server-side receiving section for receiving the information transmitted from the terminal through the communication network;
a first peak candidate searching section for searching for a first peak candidate by searching for a signal differential value (A) having a maximum absolute value in the signal differential values at the respective temperatures received by the server-side receiving section as the first peak candidate;
a first peak determining section for determining that the signal differential value (A) is the first peak when a temperature ($t_1$) indicating the signal differential value (A) is included in a temperature range ($T_1$) that is either one of the temperature range ($T_H$) and the temperature range ($T_L$) and there is no peak when the temperature ($t_1$) indicating the signal differential value (A) is not included in either the temperature range ($T_H$) or the temperature range ($T_L$);
a second peak candidate searching section for, when the first peak is present, conducting a search from the temperature range ($T_1$) that is one of the temperature range ($T_H$) and the temperature range ($T_L$) in which the temperature ($t_1$) is included toward a temperature range ($T_2$) that is the other one thereof with the temperature ($t_1$) indicating the signal differential value (A) being as a starting point, to find a signal differential value (C) lying immediately before or after an absolute value of a signal differential value changes from decreasing to increasing and having a minimum absolute value, and a signal differential value (D) that is to be a second peak candidate lying immediately before or after an absolute value of a signal differential value changes from increasing to decreasing and having an absolute value that is greatest next to the absolute value of the signal differential value (A) among the signal differential values at the respective temperatures received by the server-side receiving section;
a first second-peak determining section for determining that the signal differential value (D) is the second peak candidate when the signal differential value (C) and the signal differential value (D) are present and there is no second peak when the signal differential value (C) and the signal differential value (D) are not present;
an X calculating section for performing calculation of the formula "$X=(A-C)/(D-C)$" using the signal differential value (A), the signal differential value (C), and the signal differential value (D);
a second second-peak determining section for determining a second peak by determining that the signal differential value (D) is the second peak when X satisfies a condition [X<predetermined threshold value] and a temperature ($t_2$) indicating the signal differential value (D) is included in the other temperature range ($T_2$) and there is no second peak when X satisfies the condition [X<predetermined threshold value] and the temperature ($t_2$) indicating the signal differential value (D) is not included in the other temperature range ($T_2$);
an integral value calculating section for calculating, when X satisfies a condition [X$\geq$predetermined threshold value], an integral value ($Y_1$) of signal differential values in the one temperature range ($T_1$) including the temperature ($t_1$) by integrating the signal differential values in the one temperature range ($T_1$) and an integral value ($Y_2$) of signal differential values in the other temperature range ($T_2$) including the temperature ($t_2$) by integrating the signal differential values in the other temperature range ($T_2$);
a Y calculating section for performing calculation of the following formula using the integral value ($Y_1$) of the signal differential values in the one temperature range ($T_1$) and the integral value ($Y_2$) of the signal differential values in the other temperature range ($T_2$):

$$Y=Y_1/Y_2; \text{ and}$$

a third second-peak determining section for determining that the signal differential value (D) is the second peak when Y satisfies a condition [$1 \leq Y$'predetermined threshold value] and there is no second peak when Y satisfies a condition [Y>predetermined threshold value] or a condition [Y<1]. In the system, at least the signal differential values at the respective temperatures are transmitted from the terminal-side transmitting section to the server-side receiving section, and information of the determination results as to the first peak and the second peak are transmitted from the server-side transmitting section to the terminal-side receiving section.

The terminal preferably further includes: a differential value calculating section for calculating signal differential values at respective temperatures by differentiating the signal values showing the molten states of the sample at the respective temperatures. In the case where the signal values before being differentiated are transmitted from the terminal to the server, the server preferably includes the differential value calculating section.

The terminal or the server preferably further includes: a polynomial value calculating section for calculating polynomial values of the signal differential values at the respective temperatures by performing polynomial calculation of the respective signal differential values. It is preferable that the polynomial values of the signal differential values at the respective temperatures calculated in the polynomial value calculating section are used as the signal differential values at respective temperatures in other sections. In addition, the terminal or the server may further include a moving average calculating section for calculating moving average values of the signal differential values at the respective temperatures by conducting moving average calculation with respect to the signal differential values at the respective temperatures. Furthermore, in the other sections, the moving average values of the signal differential values at the respective temperatures calculated in the moving average value calculating section also can be used as, for example, the signal differential values at the respective temperatures.

The network melting curve analyzing system of the present invention preferably is a system for analyzing a melting curve of a double-stranded nucleic acid, and the double-stranded nucleic acid preferably is composed of a target nucleic acid having a target site and a nucleic acid that can hybridize to the target site. A polymorphism in the target site preferably is analyzed by analyzing the melting curve of the double-stranded nucleic acid composed of the target nucleic acid having the target site and the nucleic acid that can hybridize to the target site.

In the present invention, in the case where the target nucleic acid is a pair of alleles, when it is determined that there is no second peak, it preferably is determined further that the polymorphism in the target site is homozygous, and when it is determined that the signal differential value (D) is the second peak, it is preferably further determined that the polymorphism in the target site is heterozygous by the first second-peak determining section, the second second-peak determining section, and the third second-peak determining section.

The server preferably further includes a polymorphism determining section for determining whether a polymorphism in a target site of the target nucleic acid is of a wild type or of a mutant type. The determining method is the same as described above. In this case, information of the determination result as to the polymorphism is preferably transmitted from the server to the terminal. The terminal may include the polymorphism determining section, and the polymorphism may be determined based on the information of the determination result as to the first peak and the second peak transmitted from the server to the terminal.

The terminal of the present invention is a terminal used for the network melting curve analyzing system of the present invention. The terminal includes:
a differential value input section for inputting differential values of signal values showing molten states of a sample at respective temperatures;
a terminal-side transmitting section for transmitting information in the terminal to the server through the communication network; and
a terminal-side receiving section for receiving the information transmitted from the server through the communication network. In the terminal, at least the signal differential values at the respective temperatures are transmitted from the terminal-side transmitting section to the server-side receiving section, and information of the determination result as to the first peak is transmitted from the server-side transmitting section to the terminal-side receiving section. Further, from the server-side transmitting section, information of the determination result as to the second peak is preferably transmitted to the terminal-side receiving section in addition to the determination result as to the first peak.

<Second Peak Determining System>

A second peak determining system of the present invention is a second peak determining system for determining, when a peak (a first peak) is present in a temperature range ($T_1$) that is either one of a relatively high predetermined temperature range ($T_H$) and a relatively low predetermined temperature range ($T_L$) in a melting curve of a sample, whether or not a peak (a second peak) is present in a temperature range ($T_2$) that is the other one of the temperature range ($T_H$) and the temperature range ($T_L$), including: a differential value input section for inputting differential values of signal values showing molten states of the sample at respective temperatures;
an integral value calculating section for calculating an integral value ($Y_1$) of signal differential values in the one temperature range ($T_1$) by integrating the signal differential values in the one temperature range ($T_1$) and an integral value ($Y_2$) of signal differential values in the other temperature range ($T_2$) by integrating the signal differential values in the other temperature range ($T_2$);
a Y calculating section for performing calculation of the formula "$Y=Y_1/Y_2$" using the integral value ($Y_1$) of the signal differential values in the one temperature range ($T_1$) and the integral value ($Y_2$) of the signal differential values in the other temperature range ($T_2$); and
a second peak determining section for determining that there is the second peak when Y satisfies a condition [$1 \leq Y \leq$ predetermined threshold value] and there is no second peak when Y satisfies a condition [Y>predetermined threshold value] or a condition [Y<1].

The second peak determining system of the present invention preferably further includes: a second peak candidate searching section for conducting a search from the temperature range ($T_1$) in which the temperature ($t_1$) is included toward the other temperature range ($T_2$) with the temperature ($t_1$) indicating the first peak being as a starting point, to find a signal differential value (C) lying immediately before or after an absolute value of a signal differential value changes from decreasing to increasing and having a minimum absolute value, and, as a second peak candidate, a signal differential value (D) lying immediately before or after an absolute value of a signal differential value changes from increasing to decreasing and having an absolute value that is greatest next to the absolute value of the signal differential value (A) among the signal differential values at the respective temperatures inputted by the differential value input section. For example, in the case where the signal differential value (C) and the signal differential value (D) are present, it is preferable that the Y calculating section and the second peak determining section are executed, whereby it is determined that the signal differential value (D) is the second peak by the second peak determining section when Y satisfies a condition [$1 \leq Y \leq$ predetermined threshold value]. On the other hand, in the case where the signal differential value (C) and the signal differential value (D) are not present, it can be determined that there is no second peak by the second peak determining section, for example. The second peak candidate searching section corresponds to, for example, the second peak candidate searching section in the melting curve analyzing system of the present invention.

The second peak determining system of the present invention further may include:

an X calculating section for performing calculation of the formula "X=(A−C)/(D−C)" using the signal differential value (A), the signal differential value (C), and the signal differential value (D); and a determining section for determining that the signal differential value (D) is the second peak when X satisfies a condition [X<predetermined threshold value] and a temperature ($t_2$) indicating the signal differential value (D) is included in the other temperature range ($T_2$) and there is no second peak when X satisfies the condition [X<predetermined threshold value] and the temperature ($t_2$) indicating the signal differential value (D) is not included in the other temperature range ($T_2$). When X satisfies the condition [X≧predetermined threshold value], the Y calculating section preferably is executed.

The second peak determining system of the present invention preferably is used as the second second-peak determining section in the melting curve analyzing system of the present invention.

<Second Peak Determining Network System and Terminal Used Therefor>

The second peak determining system of the present invention may be a network system including a terminal and a server shown below. It is to be noted that the second peak determining network system is the same as the above-described second peak determining system unless otherwise stated. That is, the network second peak determining system of the present invention is a network second peak determining system for analyzing, when a peak (a first peak) is present in a temperature range ($T_1$) that is either one of a relatively high predetermined temperature range ($T_H$) and a relatively low predetermined temperature range ($T_L$) in a melting curve of a sample, whether or not a peak (a second peak) is present in a temperature range ($T_2$) that is the other one of the temperature range ($T_H$) and the temperature range ($T_L$), including:

a terminal; and
a server,
wherein the terminal and the server are connectable through a communication network that is outside of the system, the terminal includes:
a differential value input section for inputting differential values of signal values showing molten states of the sample at respective temperatures;
a terminal-side transmitting section for transmitting information in the terminal to the server through the communication network; and
a terminal-side receiving section for receiving the information transmitted from the server through the communication network, the server includes:
a server-side transmitting section for transmitting information in the server to the terminal through the communication network;
a server-side receiving section for receiving the information transmitted from the terminal through the communication network;
an integral value calculating section for calculating an integral value ($Y_1$) of signal differential values in the one temperature range ($T_1$) by integrating the signal differential values in the one temperature range ($T_1$) received by the server-side receiving section and an integral value ($Y_2$) of signal differential values in the other temperature range ($T_2$) by integrating the signal differential values in the other temperature range ($T_2$) received by the server-side receiving section;
a Y calculating section for performing calculation of the following formula using the integral value ($Y_1$) of the signal differential values in the one temperature range ($T_1$) and the integral value ($Y_2$) of the signal differential values in the other temperature range ($T_2$):

$Y=Y_1/Y_2$; and a second peak determining section for determining a second peak by determining that there is the second peak when Y satisfies a condition [1≦Y≦predetermined threshold value] and there is no second peak when Y satisfies a condition [Y>predetermined threshold value] or a condition [Y<1]. In the system, at least the signal differential values at the respective temperatures are transmitted from the terminal-side transmitting section to the server-side receiving section, and information of the determination result as to the second peak is transmitted from the server-side transmitting section to the terminal-side receiving section.

The server preferably further includes: a second peak candidate searching section for conducting a search from the temperature range ($T_1$) in which the temperature ($t_1$) is included toward the other temperature range ($T_2$) with the temperature ($t_1$) indicating the first peak as a starting point, to find a signal differential value (C) lying immediately before or after an absolute value of a signal differential value changes from decreasing to increasing and having a minimum absolute value, and, as a second peak candidate, a signal differential value (D) lying immediately before or after an absolute value of a signal differential value changes from increasing to decreasing and having an absolute value that is greatest next to the absolute value of the signal differential value (A) among the signal differential values at the respective temperatures inputted by the differential value input section. For example, in the case where the signal differential value (C) and the signal differential value (D) are present, it is preferable that the Y calculating section and the second peak determining section are executed, whereby it is determined that the signal differential value (D) is the second peak by the second peak determining section when Y satisfies a condition [1≦Y≦predetermined threshold value]. On the other hand, in the case where the signal differential value (C) and the signal differential value (D) are not present, it can be determined that there is no second peak.

The terminal of the present invention is a terminal used for the second peak determining system of the present invention. The terminal includes:

a differential value input section for inputting differential values of signal values showing molten states of a sample at respective temperatures;
a terminal-side transmitting section for transmitting information in the terminal to the server through the communication network; and
a terminal-side receiving section for receiving the information transmitted from the server through the communication network. In the terminal, at least the signal differential values at the respective temperatures are transmitted from the terminal-side transmitting section to the server-side receiving section, and information of the determination result as to the second peak is transmitted from the server-side transmitting section to the terminal-side receiving section.

<Melting Curve Analyzing Device>

A melting curve analyzing device of the present invention is a device for analyzing whether or not a peak is present in at least one of a relatively high predetermined temperature range ($T_H$) and a relatively low predetermined temperature range ($T_L$) in a melting curve of a sample, including the melting curve analyzing system of the present invention.

<Second Peak Determining Device>

A second peak determining device of the present invention is a second peak determining device for determining, when a peak (a first peak) is present in a temperature range ($T_1$) that is either one of a relatively high predetermined temperature range ($T_H$) and a relatively low predetermined temperature range ($T_L$) in a melting curve of a sample, whether or not a peak (a second peak) is present in a temperature range ($T_2$) that is the other one of the temperature range ($T_H$) and the temperature range ($T_L$), including the second peak determining system of the present invention. The second peak determining device of the present invention preferably is used for the melting curve analyzing device of the present invention.

<Program>

A program of the present invention is a computer program that can execute the melting curve analyzing method of the present invention on a computer. Further, the program of the present invention is a computer program that can execute the second peak determining method of the present invention on a computer.

<Electronic Medium>

An electronic medium of the present invention is an electronic medium storing the computer program of the present invention.

Next, examples of the present invention will be explained.

First Example of System Configuration

Figure 3:
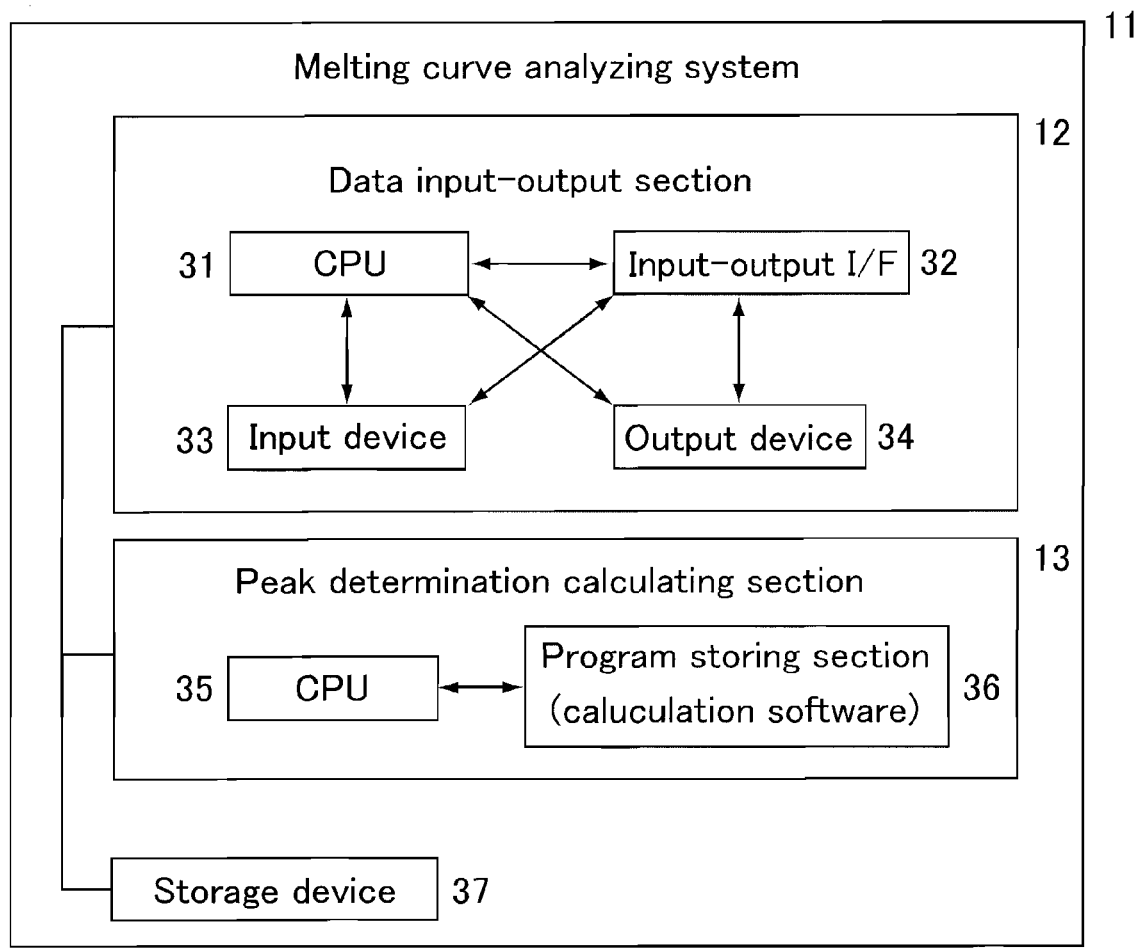
FIG. 3 is a block diagram showing one example of a configuration of the stand-alone type device.

FIG. 1 shows an overall configuration of a stand-alone type system as one example of a configuration of a system of the present invention. The system shown in FIG. 1 includes a melting curve analyzing system 11 of the present invention, and the melting curve analyzing system 11 includes a data input-output section 12 and a peak determination calculating section 13. FIG. 3 shows one example of a hardware configuration of a stand-alone type melting curve analyzing device. As shown in FIG. 3, the melting curve analyzing system 11 includes a data input-output section 12, a peak determination calculating section 13, and a storage device 37. The data input-output section 12 includes computer equipment including a CPU 31 for running a program, an input-output I/F (interface) 32, an input device 33 for inputting data, and an output device 34 for outputting data. Examples of the input device 33 include a keyboard, a mouse, and the like, and examples of the output device 34 include a printer, a LED or a liquid crystal display, and the like. The peak determination calculating section 13 includes computer equipment including a program storing section 36 in which a program is stored and a CPU 35 for running the program. In the storage device 37, for example, the data such as signal values and signal differential values at respective temperatures, Tm values ($Tm_H$ value, $Tm_L$ value) and predetermined temperature ranges including the Tm values ($T_H$, $T_L$), the type of a detection probe (a wild-type detection probe or a mutant-type detection probe) and the sequence thereof, and the like are stored in the call ready state. Examples of the storage device 37 include a ROM, a HDD, a HD, and the like, and the storage device 37 stores data while controlling reading/writing under the control of the CPU. It is to be noted that the data input-output section 12, the peak determination calculating section 13, and the storage device 37 are merely functional, and for example, they may be configured integrally in one set of computer equipment or configured individually in multiple sets of computer equipment.

Further, the system of the present invention further may include a temperature changing treatment section for changing a temperature of the sample, and a detection section for detecting signal values showing molten states of the sample during a temperature changing treatment continuously and intermittently. Furthermore, the signal values detected in the detection section may be inputted by the data input-output section. The temperature changing treatment section may be, for example, a heat treatment section for heat-treating a sample or a cooling treatment section for cooling the heated sample. Examples of the temperature changing treatment section include a heating device and the like. Examples of the detection section include an optical photometer and a fluorometer. The temperature changing treatment section and the detection section may be configured integrally in one set of computer equipment or configured individually in multiple sets of computer equipment. In addition, the system may include a nucleic acid extracting section for extracting a nucleic acid from a biological sample, an amplification treatment section for conducting a nucleic acid amplification reaction, and the like. With the foregoing configuration, it is possible to provide a genotype determining system that can conduct an operation, for example, from amplification of a nucleic acid to determination of a polymorphism by a melting curve analysis automatically within the single system.

Second Example of System Configuration

Figure 2:
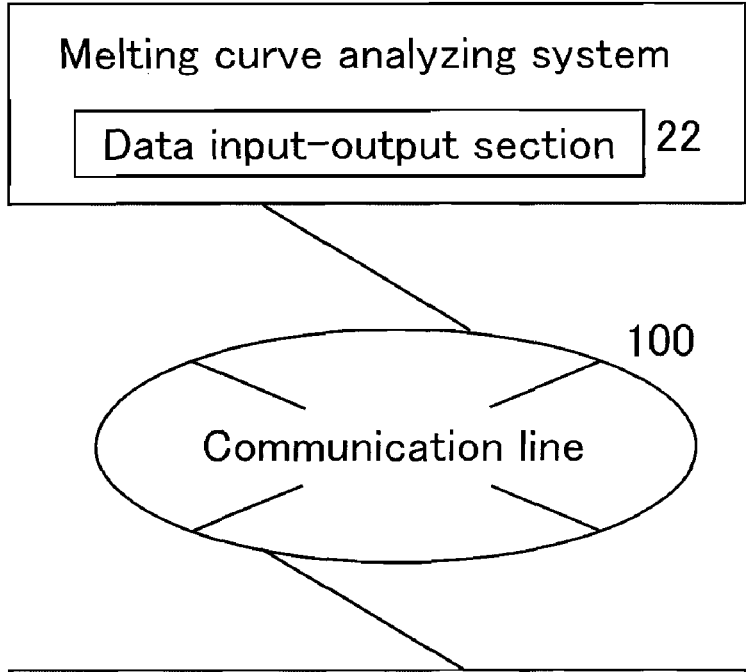
FIG. 2 shows an overall configuration of one example of a network-utilizing type device using the system of the present invention.
Figure 2:
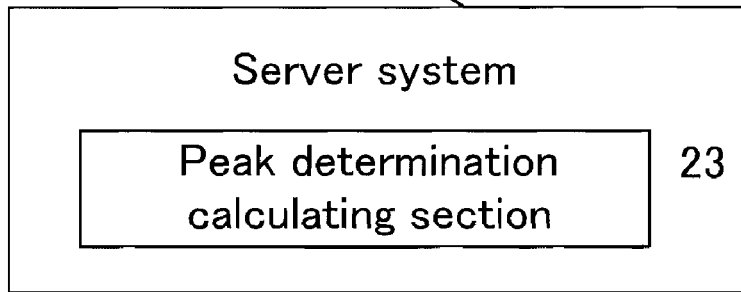
Figure 4:
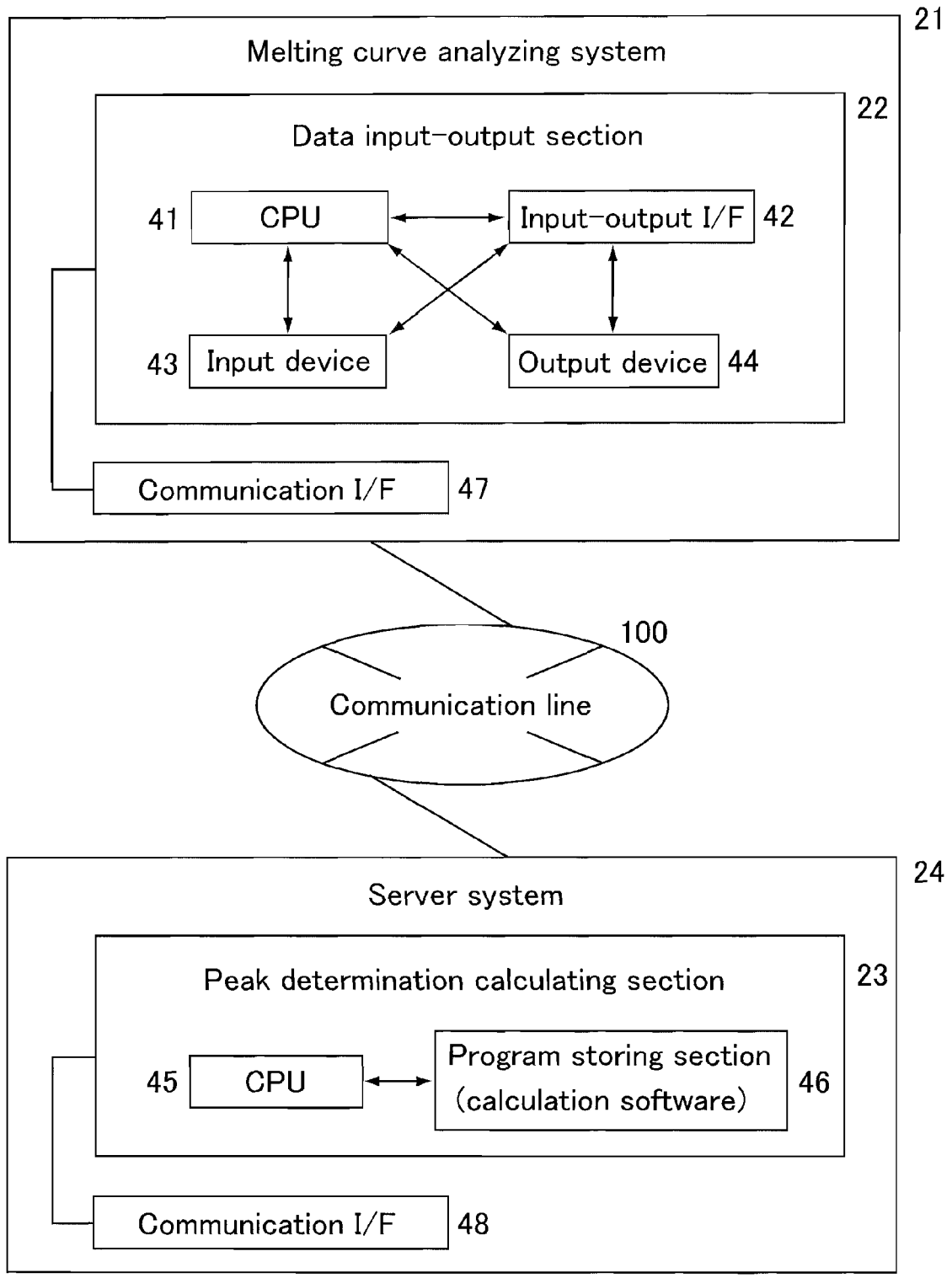
FIG. 4 is a block diagram showing one example of a configuration of the network-utilizing type device.

FIG. 2 shows an overall configuration of a network-type system that performs processing in a server. As shown in FIG. 2, the system of the present embodiment includes a melting curve analyzing system 21 of the present invention and a server system 24 including a peak determination calculating section 23. The melting curve analyzing system 21 includes a data input-output section 22. The melting curve analyzing system 21 and the server system 24 are connected through a communication line 100 such as a public network, a dedicated line, or the like that operates as the Internet based on TCP (Transmission Control Protocol)/IP (Internet Protocol). FIG. 4 shows one example of a device configuration of the network-utilizing type system. The melting curve analyzing system 21 includes the data input-output section 22 and a communication I/F (interface) 47, and is connected to the communication line 100 through the communication I/F 47. The server system 24 includes the peak determination calculating section 23 and a communication I/F 48, and is connected to the communication line 100 through the communication I/F 48. The data input-output section 22 includes a CPU 41 for running a program, an input-output I/F 42, an input device 43 for inputting data, and an output device 44 for outputting the data. The data input-output section 22 and the communication I/F 47 are merely functional, and for example, they may be configured integrally in one set of computer equipment or configured individually in multiple sets of computer equipment. The peak determination calculating section 23 includes a CPU 45 for running a program and a program storing section 46 in which the program is stored. The peak determination calculating section 23 and the communication I/F 48 are merely functional, and for example, they may be configured integrally in one set of computer equipment or configured individually in multiple sets of computer equipment.

Example of Basic Processing of System

Figure 5:
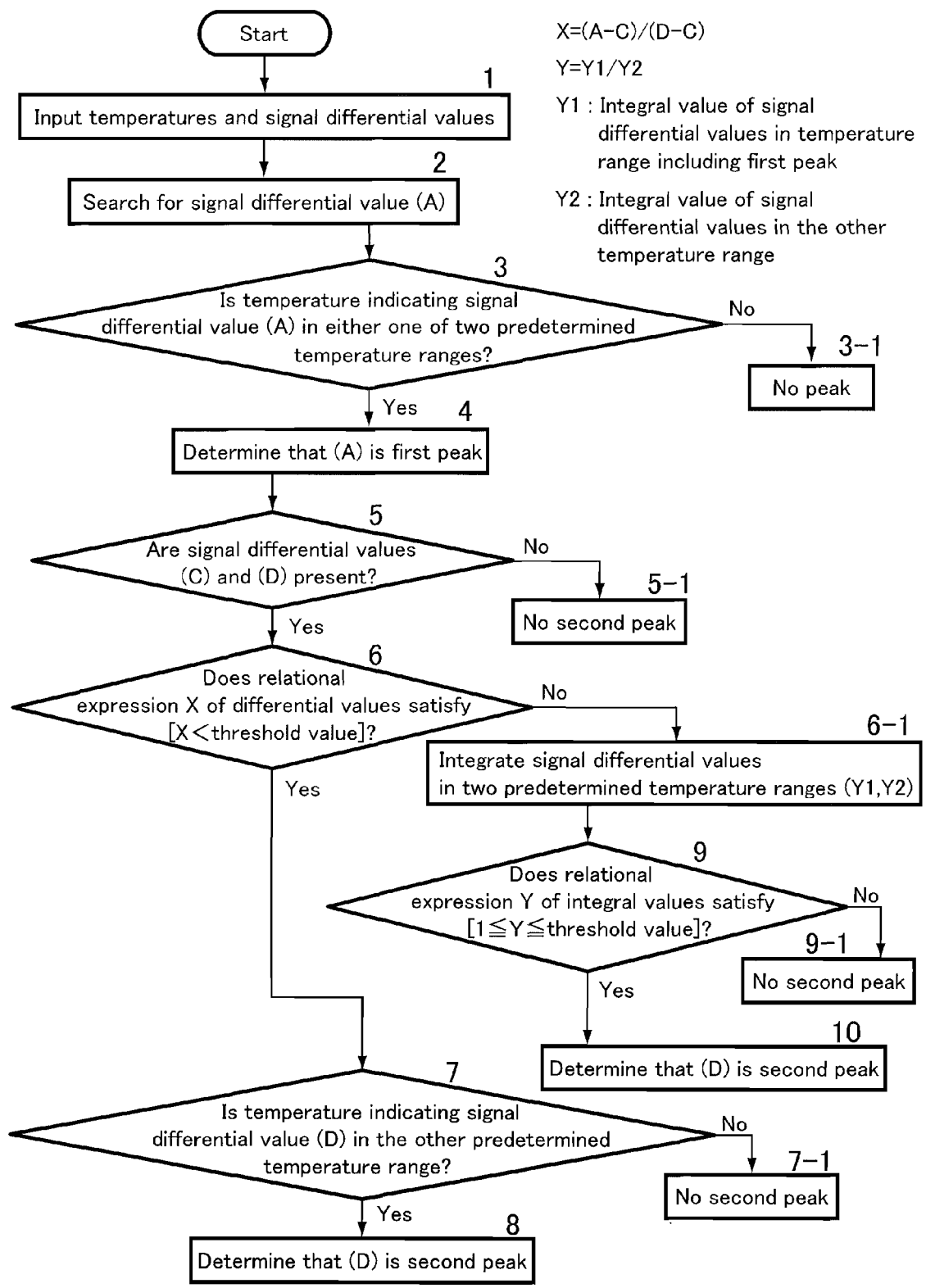
FIG. 5 shows one example of a flowchart for running the system of the present invention.

An example of basic processing of the melting curve analyzing system of the present invention is shown in a flowchart of FIG. 5. Hereinafter, the flow of the processing will be explained following FIG. 5. It is to be noted that each processing step of the system of the present invention can be carried out by using; hardware components such as a CPU, a main memory, a bus or exterior peripheral devices like a secondary storage device, a printer, a display, and others; input-output ports (I/O ports) for the exterior peripheral devices; a driver program for controlling these hardware components and other application programs; and the like, as appropriate.

[1]
Signal differential values at respective temperatures are inputted.

[2]
The maximum signal differential value (A) is searched for.

[3]
Whether or not a temperature indicating the signal differential value (A) is included in a temperature range ($T_1$) that is either one of a temperature range $T_H$ and a temperature range $T_L$ is determined.

[3-1; No]
When [3] is No, it is determined that there is no peak.

[4; Yes]
When [3] is Yes, it is determined that the differential value (A) is a first peak.

[5]
Whether or not a signal differential value (C) and a signal differential value (D) are present is searched for.

[5-1; No.]
When [5] is No, it is determined that there is no second peak.

[6]
When [5] is Yes, whether or not X calculated from the signal differential values (A), (C), and (D) satisfies a condition [X>threshold value] is determined.

[7: Yes]
When [6] is Yes, whether or not a temperature indicating the signal differential value (D) is included in the other one of the temperature range ($T_H$) and the temperature range ($T_L$), which is a temperature range ($T_2$) that is not the temperature range ($T_1$), is determined.

[7-1: No]
When [7] is No, it is determined that there is no second peak.

[8: Yes]
When [7] is Yes, it is determined that the signal differential value (D) is a second peak.

[6-1: No]
When [6] is No, an integrated value ($Y_1$) in the temperature range ($T_1$) is calculated by adding up the signal differential values in the temperature range ($T_1$), and an integrated value ($Y_2$) in the temperature range ($T_2$) is calculated by adding up the signal differential values in the temperature range ($T_2$).

[9]
Y is calculated by performing calculation using the integrated value ($Y_1$) in the temperature range ($T_1$) and the integrated value ($Y_2$) in the temperature range ($T_2$), and whether or not Y satisfies a condition [$1 \leq Y \leq$ predetermined threshold value] is determined.

[9-1: No]
When [9] is No, it is determined that there is no second peak.

[10: Yes]
When [9] is Yes, it is determined that the signal differential value (D) is the second peak.

Figure 6:
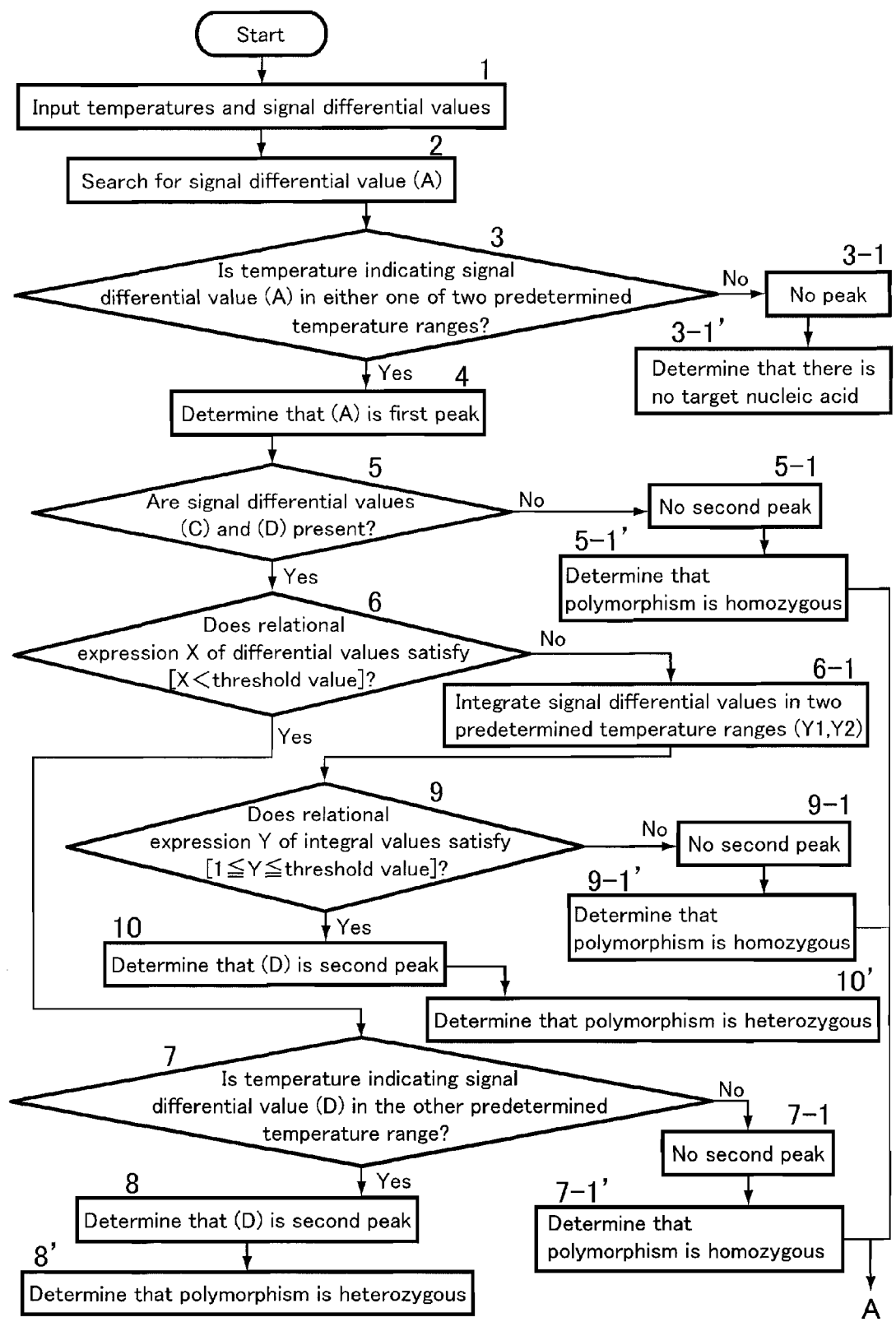
FIG. 6 shows another example of a flowchart for running the system of the present invention.

Further, the flowchart of FIG. 6 shows an example of processing for determining whether a polymorphism is homozygous or heterozygous from the determination result as to the presence or absence of the first peak and the second peak. The flowchart is the same as that of FIG. 5 unless otherwise stated.

[3-1']
When it is determined that there is no peak in [3-1], it is determined that there is no target nucleic acid.

[5-1']
When it is determined that there is no second peak in [5-1], it is determined that a polymorphism is homozygous.

[7-1']
When it is determined that there is no second peak in [7-1], it is determined that the polymorphism is homozygous.

[8']
When it is determined that the signal differential value (D) is the second peak in [8], it is determined that the polymorphism is heterozygous.

[9-1']
When it is determined that there is no second peak in [9-1], it is determined that the polymorphism is homozygous.

[10']
When it is determined that the signal differential value (D) is the second peak in [10], it is determined that the polymorphism is heterozygous.

Figure 7A:
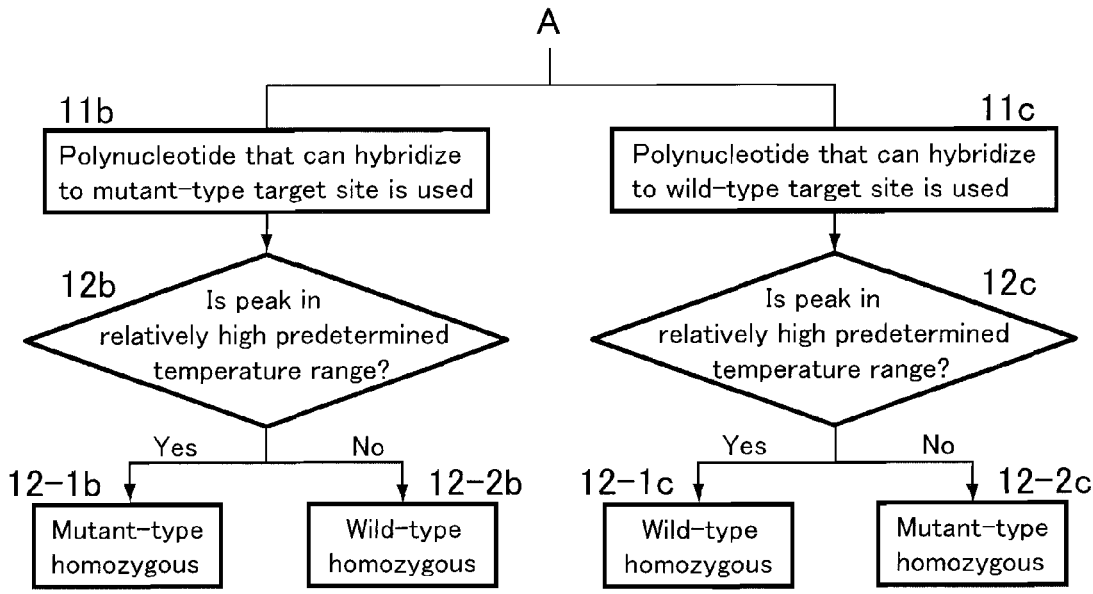
FIG. 7 shows yet another example of a flowchart for running the system of the present invention.
Figure 7B:
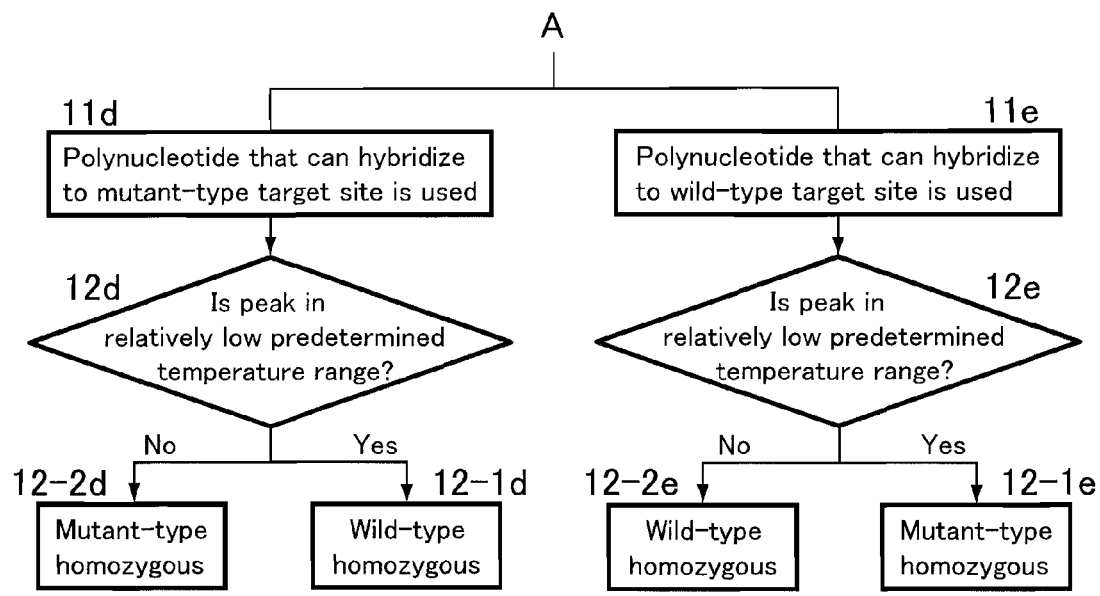

Further, the flowcharts of FIGS. 7A and 7B show an example of processing for determining whether a polymorphism is of a wild type or a mutant type when the polymorphism is determined as homozygous from the determination result that there is no second peak. The flowcharts are the same as those of FIGS. 5 and 6 unless otherwise stated. It is to be noted that flowcharts of FIGS. 7A and 7B is the flowcharts following "A" in FIG. 6.

Determination is made as below depending on the type of a detection nucleic acid.

[11b]
The detection nucleic acid is a mutant-type detection polynucleotide (a mutant-type detection nucleic acid).

[12b]
Whether or not a temperature indicating the first peak is included in the temperature range $T_H$ is determined.

[12-1b: Yes]
When [12b] is Yes, it is determined that the polymorphism is a mutant-type homozygote.

[12-2b: No]
When [12b] is No, it is determined that the polymorphism is a wild-type homozygote.

[11c]
The detection nucleic acid is a wild-type detection polynucleotide (a wild-type detection nucleic acid).

[12c]
Whether or not a temperature indicating the first peak is included in the temperature range $T_H$ is determined.

[12-1c: Yes]
When [12c] is Yes, it is determined that the polymorphism is a wild-type homozygote.

[12-2c: No]
When [12c] is No, it is determined that the polymorphism is a mutant-type homozygote.

[11d]
The detection nucleic acid is a mutant-type detection polynucleotide (a mutant-type detection nucleic acid).

[12d]
Whether or not a temperature indicating the first peak is included in the temperature range $T_L$ is determined.

[12-1d: Yes]
When [12d] is Yes, it is determined that the polymorphism is a wild-type homozygote.

[12-2d: No]
When [12d] is No, it is determined that the polymorphism is a mutant-type homozygote.

[11e]
The detection nucleic acid is a wild-type detection polynucleotide (a wild-type detection nucleic acid).
[12e]
Whether or not a temperature indicating the first peak is included in the temperature range $T_L$ is determined.
[12-1e: Yes]
When [12e] is Yes, it is determined that the polymorphism is a mutant-type homozygote.
[12-2e: No]
When [12e] is No, it is determined that the polymorphism is a wild-type homozygote.

Industrial Applicability

As above, according to the present invention, the presence or absence of a peak in at least one of two predetermined temperature ranges in a melting curve can be analyzed by utilizing the calculation described above. Therefore, since the conventional problems that criteria of determination vary between individuals who conduct analyses and specialized knowledge is required do not occur, it becomes possible to easily analyze a melting curve and also to automate the analysis. Therefore, for example, the present invention can be used also in the field of general analysis and diagnosis, and the present invention allows the analysis with respect to a large number of specimens to be conducted. Thus, it can be said that the present invention is very useful technology especially in the field of gene analysis.

The invention claimed is:

1. A melting curve analyzing method for analyzing whether or not a peak is present in at least one of a relatively high predetermined temperature range ($T_H$) and a relatively low predetermined temperature range ($T_L$) in a melting curve of a sample, comprising:
   a step of providing differential values of signal values showing molten states of the sample at respective temperatures;
   a step of searching for a first peak candidate by searching using a computer for a signal differential value (A) having a maximum absolute value in the signal differential values at the respective temperatures as the first peak candidate; and
      a step of determining a first peak by determining that the signal differential value (A) is the first peak when a temperature ($t_1$) indicating the signal differential value (A) is included in a temperature range ($T_1$) that is either one of the temperature range ($T_H$) and the temperature range ($T_L$) and there is no peak when the temperature ($t_1$) indicating the signal differential value (A) is not included in either the temperature range ($T_H$) or the temperature range ($T_L$).

2. The melting curve analyzing method according to claim 1, for further analyzing, when it is determined that the first peak is present, whether or not a second peak is present in the other temperature range in which the first peak is not present, the method further comprising:
   a step of searching for a second peak candidate, the step including: conducting a search from the temperature range ($T_1$) that is one of the temperature range ($T_H$) and the temperature range ($T_L$) in which the temperature ($t_1$) is included toward a temperature range ($T_2$) that is the other one thereof with the temperature ($t_1$) indicating the signal differential value (A) as a starting point, to find a signal differential value (C) lying immediately before or after an absolute value of a signal differential value changes from decreasing to increasing and having a minimum absolute value, and a signal differential value (D) that is to be a second peak candidate lying immediately before or after an absolute value of a signal differential value changes from increasing to decreasing and having an absolute value that is greatest next to the absolute value of the signal differential value (A) among the signal differential values at the respective temperatures; and
   a first step of determining a second peak by determining that there is no second peak when the signal differential value (C) and the signal differential value (D) are not present.

3. The melting curve analyzing method according to claim 2, wherein when the signal differential value (C) and the signal differential value (D) are present, the method further comprises:
   a step of calculating X by performing calculation of the following formula using the signal differential value (A), the signal differential value (C), and the signal differential value (D):

$$X = (A-C)/(D-C); \text{ and}$$

a second step of determining a second peak by determining that the signal differential value (D) is the second peak when X satisfies a condition [X<predetermined threshold value] and a temperature ($t_2$) indicating the signal differential value (D) is included in the other temperature range ($T_2$) and there is no second peak when X satisfies the condition [X<predetermined threshold value] and the temperature ($t_2$) indicating the signal differential value (D) is not included in the other temperature range ($T_2$).

4. The melting curve analyzing method according to claim 3, wherein when X satisfies a condition [X≧threshold value], the method further comprises:
   a step of calculating an integral value ($Y_1$) of signal differential values in the one temperature range ($T_1$) including the temperature ($t_1$) by integrating the signal differential values in the one temperature range ($T_1$) and an integral value ($Y_2$) of signal differential values in the other temperature range ($T_2$) including the temperature ($t_2$) by integrating the signal differential values in the other temperature range ($T_2$);
   a step of calculating Y by performing calculation of the following formula using the integral value ($Y_1$) of the signal differential values in the one temperature range ($T_1$) and the integral value ($Y_2$) of the signal differential values in the other temperature range ($T_2$):

$$Y = Y_1/Y_2; \text{ and}$$

a third step of determining a second peak by determining that the signal differential value (D) is the second peak when Y satisfies a condition [1≦Y≦predetermined threshold value] and there is no second peak when Y satisfies a condition [Y>predetermined threshold value] or a condition [Y<1].

5. The melting curve analyzing method according to claim 1, wherein, in the differential value providing step, the signal differential values at the respective temperatures are calculated by differentiating the signal values showing the molten states of the sample at the respective temperatures.

6. The melting curve analyzing method according to claim 1, further comprising:
   a step of calculating polynomial values of the signal differential values at the respective temperatures provided in the differential value providing step by performing polynomial calculation of successive signal differential values, wherein the polynomial values of the signal differential values at the respective temperatures calculated in the polynomial value calculating step are used as the signal differential values at the respective temperatures in other steps.

7. The melting curve analyzing method according to claim 6, wherein, in the polynomial value calculating step, the polynomial values of the signal differential values at the respective temperatures are calculated by performing polynomial calculation based on the following formula with respect to the signal differential values at the respective temperatures provided in the differential value providing step:

polynomial value=$(P_{M-1}+P_M+P_{M+1})$, where in the formula,
$P_M$ is a signal differential value at an arbitrary point (M), $P_{M-1}$ is a signal differential value at a point (M−1) that is immediately before the arbitrary point (M), $P_{M+1}$ is a signal differential value at a point (M+1) that is immediately after the arbitrary point (M), and M is a positive integer of two or more.

8. A second peak determining method for determining, when a peak (a first peak) is present in a temperature range $(T_1)$ that is either one of a relatively high predetermined temperature range $(T_H)$ and a relatively low predetermined temperature range $(T_L)$ in a melting curve of a sample, whether or not a peak (a second peak) is present in a temperature range $(T_2)$ that is the other one of the temperature range $(T_H)$ and the temperature range (TO, comprising:
a step of providing differential values of signal values showing molten states of the sample at respective temperatures;
a step of calculating using a computer an integral value $(Y_1)$ of signal differential values in the one temperature range $(T_1)$ by integrating the signal differential values in the one temperature range $(T_1)$ and an integral value $(Y_2)$ of signal differential values in the other temperature range $(T_2)$ by integrating the signal differential values in the other temperature range $(T_2)$;
a step of calculating Y by performing calculation of the following formula using the integral value $(Y_1)$ of the signal differential values in the one temperature range $(T_1)$ and the integral value $(Y_2)$ of the signal differential values in the other temperature range $(T_2)$:

$Y=Y_1/Y_2$; and a step of determining a second peak by determining that there is the second peak when Y satisfies a condition [1≦Y≦predetermined threshold value] and there is no second peak when Y satisfies a condition [Y>predetermined threshold value] or a condition [Y<1].

9. A melting curve analyzing system for analyzing whether or not a peak is present in at least one of a relatively high predetermined temperature range $(T_H)$ and a relatively low predetermined temperature range $(T_L)$ in a melting curve of a sample, comprising:
a differential value input section for inputting differential values of signal values showing molten states of the sample at respective temperatures;
a first peak candidate searching section for searching for a first peak candidate by searching for a signal differential value (A) having a maximum absolute value in the signal differential values at the respective temperatures inputted by the differential value input section as the first peak candidate; and a first peak determining section for determining a first peak by determining that the signal differential value (A) is the first peak when a temperature $(t_1)$ indicating the signal differential value (A) is included in a temperature range $(T_1)$ that is either one of the temperature range $(T_H)$ and the temperature range $(T_L)$ and there is no peak when the temperature $(t_1)$ indicating the signal differential value (A) is not included in either the temperature range $(T_H)$ or the temperature range $(T_L)$.

10. The melting curve analyzing system according to claim 9 for further analyzing, when it is determined that the first peak is present, whether or not a second peak is present in the other temperature range in which the first peak is not present, further comprising:
a second peak candidate searching section for conducting a search from the temperature range $(T_1)$ that is one of the temperature range $(T_H)$ and the temperature range $(T_L)$ in which the temperature $(t_1)$ is included toward a temperature range $(T_2)$ that is the other one thereof with the temperature $(t_1)$ indicating the signal differential value (A) as a starting point, to find a signal differential value (C) lying immediately before or after an absolute value of a signal differential value changes from decreasing to increasing and having a minimum absolute value, and a signal differential value (D) that is to be a second peak candidate lying immediately before or after an absolute value of a signal differential value changes from increasing to decreasing and having an absolute value that is greatest next to the absolute value of the signal differential value (A) among the signal differential values at the respective temperatures inputted by the differential value input section; and
a first second-peak determining section for determining that there is no second peak when the signal differential value (C) and the signal differential value (D) are not present.

11. The melting curve analyzing system according to claim 10, further comprising:
an X calculating section for performing calculation of the following formula using the signal differential value (A), the signal differential value (C), and the signal differential value (D):

$X=(A-C)/(D-C)$; and a second second-peak determining section for determining that the signal differential value (D) is the second peak when X satisfies a condition [X<predetermined threshold value] and a temperature $(t_2)$ indicating the signal differential value (D) is included in the other temperature range $(T_2)$ and there is no second peak when X satisfies the condition [X<predetermined threshold value] and the temperature $(t_2)$ indicating the signal differential value (D) is not included in the other temperature range $(T_2)$.

12. The melting curve analyzing system according to claim 11, further comprising:
an integral value calculating section for calculating an integral value $(Y_1)$ of signal differential values in the one temperature range $(T_1)$ including the temperature $(t_1)$ by integrating the signal differential values in the one temperature range $(T_1)$ and an integral value $(Y_2)$ of signal differential values in the other temperature range $(T_2)$ including the temperature $(t_2)$ by integrating the signal differential values in the other temperature range $(T_2)$;
a Y calculating section for performing calculation of the following formula using the integral value $(Y_1)$ of the signal differential values in the one temperature range ($T_1$) and the integral value ($Y_2$) of the signal differential values in the other temperature range ($T_2$):

$$Y=Y_1/Y_2; \text{ and}$$

a third second-peak determining section for determining that the signal differential value (D) is the second peak when Y satisfies a condition [$1 \leq Y \leq$ predetermined threshold value] and there is no second peak when Y satisfies a condition [Y>predetermined threshold value] or a condition [Y<1].

13. The melting curve analyzing system according to claim 9, for analyzing whether or not a peak is present in each one of a relatively high predetermined temperature range ($T_H$) and a relatively low predetermined temperature range ($T_L$) in the melting curve of a sample, comprising:

a differential value input section for inputting differential values of signal values showing molten states of the sample at respective temperatures;

a first peak candidate searching section for searching for a first peak candidate by searching for a signal differential value (A) having a maximum absolute value in the signal differential values at the respective temperatures inputted by the differential value input section as the first peak candidate;

a first peak determining section for determining that the signal differential value (A) is the first peak when a temperature ($t_1$) indicating the signal differential value (A) is included in a temperature range ($T_1$) that is either one of the temperature range ($T_H$) and the temperature range ($T_L$) and there is no peak when the temperature ($t_1$) indicating the signal differential value (A) is not included in either the temperature range ($T_H$) or the temperature range ($T_L$);

a second peak candidate searching section for, when the first peak is present, conducting a search from the temperature range ($T_1$) that is one of the temperature range ($T_H$) and the temperature range ($T_L$) in which the temperature ($t_1$) is included toward a temperature range ($T_2$) that is the other one thereof with the temperature ($t_1$) indicating the signal differential value (A) being as a starting point, to find a signal differential value (C) lying immediately before or after an absolute value of a signal differential value changes from decreasing to increasing and having a minimum absolute value, and a signal differential value (D) that is to be a second peak candidate lying immediately before or after an absolute value of a signal differential value changes from increasing to decreasing and having an absolute value that is greatest next to the absolute value of the signal differential value (A) among the signal differential values at the respective temperatures inputted by the differential value input section;

a first second-peak determining section for determining that the signal differential value (D) is the second peak candidate when the signal differential value (C) and the signal differential value (D) are present and there is no second peak when the signal differential value (C) and the signal differential value (D) are not present;

an X calculating section for performing calculation of the following formula using the signal differential value (A), the signal differential value (C), and the signal differential value (D):

$$X=(A-C)/(D-C);$$

a second second-peak determining section for determining that the signal differential value (D) is the second peak when X satisfies a condition [X<predetermined threshold value] and a temperature ($t_2$) indicating the signal differential value (D) is included in the other temperature range ($T_2$) and there is no second peak when X satisfies the condition [X<predetermined threshold value] and the temperature ($t_2$) indicating the signal differential value (D) is not included in the other temperature range ($T_2$);

an integral value calculating section for calculating, when X satisfies a condition [X$\geq$predetermined threshold value], an integral value ($Y_1$) of signal differential values in the one temperature range ($T_1$) including the temperature ($t_1$) by integrating the signal differential values in the one temperature range ($T_1$) and an integral value ($Y_2$) of signal differential values in the other temperature range ($T_2$) including the temperature ($t_2$) by integrating the signal differential values in the other temperature range ($T_2$);

a Y calculating section for performing calculation of the following formula using the integral value ($Y_1$) of the signal differential values in the one temperature range ($T_1$) and the integral value ($Y_2$) of the signal differential values in the other temperature range ($T_2$):

$$Y=Y_1/Y_2; \text{ and}$$

a third second-peak determining section for determining that the signal differential value (D) is the second peak when Y satisfies a condition [$1 \leq Y \leq$ predetermined threshold value] and there is no second peak when Y satisfies a condition [Y>predetermined threshold value] or a condition [Y<1].

14. The melting curve analyzing system according to claim 9, further comprising:

a differential value calculating section for calculating the signal differential values at the respective temperatures by differentiating the signal values showing the molten states of the sample at the respective temperatures.

15. The melting curve analyzing system according to claim 9, further comprising:

a polynomial value calculating section for calculating polynomial values of the signal differential values at the respective temperatures inputted by the differential value input section by performing polynomial calculation of successive signal differential values, wherein the polynomial values of the signal differential values at the respective temperatures calculated in the polynomial value calculating section are used as the signal differential values at the respective temperatures in other sections.

16. The melting curve analyzing system according to claim 15, wherein, in the polynomial value calculating section, the polynomial values of the signal differential values at the respective temperatures are calculated by performing polynomial calculation based on the following formula with respect to the signal differential values at the respective temperatures inputted by the differential value input section:

$$\text{polynomial value}=(P_{M-1}+P_M+P_{M+1}),$$

where in the formula, $P_M$ is a signal differential value at an arbitrary point (M), $P_{M-1}$ is a signal differential value at a point (M−1) that is immediately before the arbitrary point (M), $P_{M+1}$ is a signal differential value at a point (M+1) that is immediately after the arbitrary point (M), and M is a positive integer of two or more.

17. A second peak determining system for determining, when a peak (a first peak) is present in a temperature range ($T_1$) that is either one of a relatively high predetermined temperature range ($T_H$) and a relatively low predetermined temperature range ($T_L$) in a melting curve of a sample, whether or not a peak (a second peak) is present in a temperature range ($T_2$) that is the other one of the temperature range ($T_H$) and the temperature range ($T_L$), comprising:
- a differential value input section for inputting differential values of signal values showing molten states of the sample at respective temperatures;
- an integral value calculating section for calculating an integral value ($Y_1$) of signal differential values in the one temperature range ($T_1$) by integrating the signal differential values in the one temperature range ($T_1$) and an integral value ($Y_2$) of signal differential values in the other temperature range ($T_2$) by integrating the signal differential values in the other temperature range ($T_2$);
- a Y calculating section for performing calculation of the following formula using the integral value ($Y_1$) of the signal differential values in the one temperature range ($T_1$) and the integral value ($Y_2$) of the signal differential values in the other temperature range ($T_2$):

$$Y = Y_1/Y_2;\text{ and}$$

- a second peak determining section for determining a second peak by determining that there is the second peak when Y satisfies a condition [$1 \leq Y \leq$ predetermined threshold value] and there is no second peak when Y satisfies a condition [Y > predetermined threshold value] or a condition [Y < 1].

* * * * *